(12) United States Patent
Beaulieu et al.

(10) Patent No.: US 7,112,320 B1
(45) Date of Patent: Sep. 26, 2006

(54) SOLID WOUND HEALING FORMULATIONS CONTAINING FIBRONECTIN

(76) Inventors: Andre Beaulieu, 4045, Chemin St-Louis, Cap-Rouge, Quebec (CA) G1Y 1V7; Robert Paquin, 951, rue de la Lorraine, St-Jean-Chrysostome, Quebec (CA) G6Z 2P5; Benoit Lariviere, 312, rue Laure Conan, St-Nicholas, Quebec (CA) G7A 3L1

( * ) Notice: Subject to any disclaimer, the term of this patent is extended or adjusted under 35 U.S.C. 154(b) by 220 days.

(21) Appl. No.: 10/049,992

(22) PCT Filed: Aug. 21, 2000

(86) PCT No.: PCT/CA00/00953

§ 371 (c)(1), (2), (4) Date: Oct. 7, 2002

(87) PCT Pub. No.: WO01/13967

PCT Pub. Date: Mar. 1, 2001

Related U.S. Application Data

(60) Continuation-in-part of application No. 09/331,344, filed as application No. PCT/CA97/00966 on Dec. 12, 1997, application No. 10/049,992, which is a continuation-in-part of application No. 09/862,971, filed on May 22, 2001, which is a division of application No. 09/245,785, filed on Feb. 5, 1999, which is a division of application No. 08/879,159, filed on Jun. 19, 1997, now Pat. No. 5,877,149, which is a continuation-in-part of application No. 08/488,253, filed on Jun. 7, 1995, now Pat. No. 5,641,483.

(60) Provisional application No. 60/182,412, filed on Feb. 14, 2000, provisional application No. 60/149,958, filed on Aug. 20, 1999.

(51) Int. Cl.
*A61K 31/74* (2006.01)
*A61K 2/00* (2006.01)
*A61K 38/16* (2006.01)

(52) U.S. Cl. .................. 424/78.06; 424/426; 514/8
(58) Field of Classification Search ............ 424/78.06, 424/426; 514/8
See application file for complete search history.

(56) References Cited

U.S. PATENT DOCUMENTS

| | | | |
|---|---|---|---|
| 3,742,995 A * | 7/1973 | Confer et al. ............. 220/660 |
| 4,001,442 A | 1/1977 | Stahlberger et al. |
| 4,243,656 A | 1/1981 | Walliczek |
| 4,341,764 A * | 7/1982 | Wallace et al. ............ 424/101 |
| 4,347,841 A | 9/1982 | Benyo et al. |
| 4,361,552 A | 11/1982 | Baur, Jr. |
| 4,404,970 A * | 9/1983 | Sawyer ..................... 424/400 |
| 4,424,208 A * | 1/1984 | Wallace et al. ............ 514/21 |
| 4,455,300 A | 6/1984 | Wallace et al. ............ 424/101 |
| 4,458,678 A | 7/1984 | Yannas et al. |
| 4,570,629 A | 2/1986 | Widra |
| 4,587,284 A | 5/1986 | Luissi et al. |
| 4,594,884 A * | 6/1986 | Bondi et al. ............... 73/64.3 |
| 4,614,794 A | 9/1986 | Easton et al. |
| 4,664,105 A | 5/1987 | Dautzenberg et al. |
| 4,703,108 A | 10/1987 | Silver et al. |
| 4,740,498 A | 4/1988 | Hirao et al. ............... 514/8 |
| 4,784,989 A | 11/1988 | Hook et al. |
| 4,837,019 A | 6/1989 | Georgalas et al. ......... 424/101 |
| 4,837,285 A | 6/1989 | Berg et al. |
| 4,885,179 A * | 12/1989 | Soucie et al. ............. 426/104 |
| 4,919,939 A | 4/1990 | Baker |
| 4,925,924 A | 5/1990 | Silver et al. ............. 530/356 |
| 4,929,442 A | 5/1990 | Powell .................... 424/85.2 |
| 4,937,230 A | 6/1990 | Pickart |
| 4,937,323 A | 6/1990 | Silver et al. |
| 4,939,135 A | 7/1990 | Robertson et al. |
| 4,947,840 A | 8/1990 | Yannas et al. |
| 4,960,413 A | 10/1990 | Sagar et al. |
| 4,963,489 A | 10/1990 | Naughton et al. |
| 4,970,216 A | 11/1990 | Deckner et al. |
| 4,973,466 A * | 11/1990 | Reich ..................... 424/426 |
| 4,981,841 A | 1/1991 | Gibson |
| 4,983,580 A | 1/1991 | Gibson |
| 5,019,096 A | 5/1991 | Fox, Jr. et al. |
| 5,045,601 A | 9/1991 | Capelli et al. |
| 5,045,631 A | 9/1991 | Kimizuka et al. ......... 530/350 |
| 5,053,388 A | 10/1991 | Gibson et al. |
| 5,064,653 A | 11/1991 | Sessions et al. |
| 5,076,265 A | 12/1991 | Wokalek |
| 5,102,988 A | 4/1992 | Kimizuka et al. ......... 530/350 |
| 5,124,155 A | 6/1992 | Reich ..................... 424/428 |
| 5,124,392 A | 6/1992 | Robertson et al. |
| 5,128,321 A | 7/1992 | Murray et al. |
| 5,143,071 A | 9/1992 | Keusch et al. |

(Continued)

FOREIGN PATENT DOCUMENTS

AU      573626      6/1988

(Continued)

OTHER PUBLICATIONS

Chemical Abstract 110,060, "Further contribution to the absorption of the active ingredient of Arthofluor ointment" (1982).*

(Continued)

*Primary Examiner*—Vickie Kim
(74) *Attorney, Agent, or Firm*—Ostrager Chong Flaherty & Broitman P.C.; Manette Dennis

(57) ABSTRACT

A concentrated solution of a wound healing promoter, in particular fibronectin, is used to develop solid wound dressings. The solid wound dressings containing fibronectin are easy to apply, easy to remove, and deliver fibronectin in a range of physiologically active dosages.

2 Claims, 6 Drawing Sheets

U.S. PATENT DOCUMENTS

| | | |
|---|---|---|
| 5,144,016 A | 9/1992 | Skjak-Braek et al. |
| 5,196,185 A | 3/1993 | Silver et al. |
| 5,196,196 A | 3/1993 | Scott et al. |
| 5,206,023 A | 4/1993 | Hunziker |
| 5,238,685 A | 8/1993 | Wren |
| 5,260,066 A | 11/1993 | Wood et al. |
| 5,270,300 A | 12/1993 | Hunziker |
| 5,271,939 A | 12/1993 | Robertson et al. |
| 5,273,900 A | 12/1993 | Boyce |
| 5,304,378 A | 4/1994 | Koga et al. |
| 5,348,939 A | 9/1994 | Horowitz et al. |
| 5,360,611 A | 11/1994 | Robertson et al. |
| 5,366,508 A | 11/1994 | Brekke |
| 5,368,858 A | 11/1994 | Hunziker |
| 5,393,602 A | 2/1995 | Urry |
| 5,395,398 A | 3/1995 | Rogozinski |
| 5,401,509 A | 3/1995 | Robertson et al. |
| 5,401,510 A | 3/1995 | Robertson et al. |
| 5,427,778 A | 6/1995 | Finkenaur et al. ....... 424/78.08 |
| 5,428,010 A | 6/1995 | Murray et al. |
| 5,441,741 A | 8/1995 | Cheong |
| 5,453,489 A | 9/1995 | Ruoslahti et al. |
| 5,453,492 A | 9/1995 | Butzow et al. |
| 5,457,093 A * | 10/1995 | Cini et al. .................... 514/12 |
| 5,462,536 A | 10/1995 | Braatz et al. |
| 5,466,462 A | 11/1995 | Rosenthal et al. |
| 5,470,576 A | 11/1995 | Patel |
| 5,480,877 A | 1/1996 | Mosher, Jr. et al. |
| 5,482,932 A | 1/1996 | Thompson |
| 5,498,600 A | 3/1996 | Murray et al. |
| 5,514,647 A | 5/1996 | Horowitz et al. |
| 5,516,896 A | 5/1996 | Murray et al. |
| 5,520,672 A | 5/1996 | Urry |
| 5,525,349 A | 6/1996 | Robertson et al. |
| 5,534,026 A | 7/1996 | Manders et al. |
| 5,567,612 A | 10/1996 | Vacanti et al. |
| 5,573,775 A | 11/1996 | Robertson et al. |
| 5,580,570 A | 12/1996 | Robertson et al. |
| 5,582,835 A | 12/1996 | Robertson et al. |
| 5,589,184 A | 12/1996 | Robertson et al. |
| 5,589,185 A | 12/1996 | Robertson et al. |
| 5,596,084 A | 1/1997 | Sanderson et al. |
| 5,599,558 A | 2/1997 | Gordinier et al. |
| 5,599,788 A | 2/1997 | Purchio et al. |
| 5,604,200 A | 2/1997 | Taylor-McCord |
| 5,604,204 A | 2/1997 | Ammann et al. |
| 5,605,938 A | 2/1997 | Roufa et al. |
| 5,607,694 A | 3/1997 | Marx |
| 5,610,148 A | 3/1997 | Brown |
| 5,613,982 A | 3/1997 | Goldstein |
| 5,624,893 A | 4/1997 | Yanni |
| 5,629,287 A | 5/1997 | Brown et al. |
| 5,629,292 A | 5/1997 | Rodgers et al. |
| 5,631,011 A | 5/1997 | Wadstrom |
| 5,631,019 A | 5/1997 | Marx |
| 5,641,483 A * | 6/1997 | Beaulieu .................. 424/78.06 |
| 5,651,982 A | 7/1997 | Marx |
| 5,654,267 A | 8/1997 | Vuori et al. |
| 5,654,270 A | 8/1997 | Ruoslahti et al. |
| 5,654,273 A | 8/1997 | Gallo et al. |
| 5,665,373 A | 9/1997 | Robertson et al. |
| 5,672,336 A | 9/1997 | Sharma |
| 5,674,524 A | 10/1997 | Scherr |
| 5,676,967 A | 10/1997 | Williams et al. |
| 5,681,568 A | 10/1997 | Goldin et al. |
| 5,686,425 A | 11/1997 | Lee |
| 5,691,423 A | 11/1997 | Smith et al. |
| 5,695,777 A | 12/1997 | Donovan et al. |
| 5,700,476 A | 12/1997 | Rosenthal et al. |
| 5,703,047 A | 12/1997 | Wilson |
| 5,705,177 A | 1/1998 | Roufa et al. |
| 5,705,178 A | 1/1998 | Roufa et al. |
| 5,709,854 A | 1/1998 | Griffith-Cima et al. |
| 5,714,588 A | 2/1998 | Purchio et al. |
| 5,716,404 A | 2/1998 | Vacanti et al. |
| 5,716,935 A | 2/1998 | Rodgers et al. |
| 5,726,058 A | 3/1998 | Jalkanen et al. |
| 5,733,563 A | 3/1998 | Fortier |
| 5,733,884 A | 3/1998 | Barbul et al. |
| 5,739,113 A | 4/1998 | Lee |
| 5,741,685 A | 4/1998 | Vacanti |
| 5,744,442 A | 4/1998 | Richards et al. |
| 5,759,570 A | 6/1998 | Arnold |
| 5,763,399 A | 6/1998 | Lee |
| 5,763,416 A | 6/1998 | Bonadio et al. |
| 5,766,631 A | 6/1998 | Arnold |
| 5,767,079 A | 6/1998 | Glaser et al. |
| 5,770,417 A | 6/1998 | Vacanti et al. |
| 5,780,244 A | 7/1998 | Engvall et al. |
| 5,782,788 A | 7/1998 | Widemire |
| 5,798,116 A | 8/1998 | Brown |
| 5,804,178 A | 9/1998 | Vacanti et al. |
| 5,820,874 A | 10/1998 | Mahoney et al. |
| 5,827,735 A | 10/1998 | Young et al. |
| 5,827,826 A | 10/1998 | Jaye et al. |
| 5,830,504 A | 11/1998 | Vuori et al. |
| 5,833,665 A | 11/1998 | Bootman et al. |
| 5,834,418 A | 11/1998 | Brazeau et al. |
| 5,834,432 A | 11/1998 | Rodgers et al. |
| 5,837,224 A | 11/1998 | Voorhees et al. |
| 5,840,777 A | 11/1998 | Eagles et al. |
| 5,843,156 A | 12/1998 | Slepian et al. |
| 5,843,182 A | 12/1998 | Goldstein |
| 5,843,741 A | 12/1998 | Wong et al. |
| 5,846,604 A | 12/1998 | Caldwell |
| 5,851,833 A | 12/1998 | Atala |
| 5,851,993 A | 12/1998 | Jalkanen et al. |
| 5,854,205 A | 12/1998 | O'Reilly et al. |
| 5,854,221 A | 12/1998 | Cao et al. |
| 5,855,610 A | 1/1999 | Vacanti et al. |
| 5,856,245 A | 1/1999 | Caldwell et al. |
| 5,863,984 A | 1/1999 | Doillon et al. |
| 5,874,164 A | 2/1999 | Caldwell |
| 5,891,558 A | 4/1999 | Bell et al. |
| 5,899,936 A | 5/1999 | Goldstein |
| 5,902,741 A | 5/1999 | Purchio et al. |
| 5,904,717 A | 5/1999 | Brekke et al. |
| 5,910,489 A | 6/1999 | Falk et al. |
| 5,919,702 A | 7/1999 | Purchio et al. |
| 5,922,676 A | 7/1999 | Pasqualini et al. |
| 5,928,633 A | 7/1999 | Fukuyama et al. |
| 5,928,635 A | 7/1999 | Schmidt |
| 5,932,207 A | 8/1999 | Schmidt |
| 5,932,552 A | 8/1999 | Blanchard et al. |
| 5,935,594 A | 8/1999 | Ringeisen et al. |
| 5,942,496 A | 8/1999 | Bonadio et al. |
| 5,945,403 A | 8/1999 | Folkman et al. |
| 5,948,432 A | 9/1999 | Timmons et al. |
| 5,955,430 A | 9/1999 | Rodgers et al. |
| 5,955,978 A | 9/1999 | Fiedler et al. |
| 5,958,874 A | 9/1999 | Clark et al. |
| 5,962,325 A | 10/1999 | Naughton et al. |
| 5,962,427 A | 10/1999 | Goldstein et al. |
| 5,965,125 A | 10/1999 | Mineau-Hanschke |
| 5,976,523 A | 11/1999 | Awaya et al. |
| 5,981,471 A | 11/1999 | Papathanassiu et al. |
| 5,981,825 A | 11/1999 | Brekke |
| 5,989,577 A | 11/1999 | Hoath et al. |
| 5,994,325 A | 11/1999 | Roufa et al. |
| 5,994,388 A | 11/1999 | Udagawa et al. |
| 6,017,727 A | 1/2000 | Jalkanen et al. |
| 6,020,326 A | 2/2000 | Roufa et al. |
| 6,024,688 A | 2/2000 | Folkman et al. |
| 6,037,139 A | 3/2000 | Greenspan et al. |

| | | | |
|---|---|---|---|
| 6,040,493 A | | 3/2000 | Cooke et al. |
| 6,048,337 A | * | 4/2000 | Svedman .................... 604/313 |
| 6,054,122 A | | 4/2000 | MacPhee et al. |
| 6,054,504 A | | 4/2000 | Dalla Riva Toma |
| 6,056,970 A | | 5/2000 | Greenawalt et al. |
| 6,071,447 A | | 6/2000 | Bootman et al. |
| 6,074,840 A | | 6/2000 | Bonadio et al. |
| 6,083,930 A | | 7/2000 | Roufa et al. |
| 6,090,911 A | | 7/2000 | Petka et al. |
| 6,093,398 A | | 7/2000 | Khaw et al. |
| 6,106,855 A | | 8/2000 | Haynes et al. |
| 6,110,208 A | | 8/2000 | Soranzo et al. |
| 6,110,487 A | | 8/2000 | Timmons et al. |
| 6,113,932 A | | 9/2000 | Hoath et al. |
| 6,117,425 A | | 9/2000 | MacPhee et al. |
| 6,123,957 A | | 9/2000 | Jernberg |
| 6,124,265 A | | 9/2000 | Timmons et al. |
| 6,124,273 A | | 9/2000 | Drohan et al. |
| 6,127,348 A | | 10/2000 | Roufa et al. |
| 6,129,761 A | | 10/2000 | Hubbell |
| 6,159,495 A | | 12/2000 | Timmons et al. |
| 6,159,496 A | | 12/2000 | Blanchard et al. |
| 6,165,496 A | | 12/2000 | Timmons et al. |
| 6,165,978 A | | 12/2000 | Rodgers et al. |
| 6,175,053 B1 | | 1/2001 | Tsubouchi |
| 6,187,743 B1 | | 2/2001 | Obi-Tabot |
| 6,190,688 B1 | | 2/2001 | Fukuyama et al. |
| 6,197,325 B1 | | 3/2001 | MacPhee et al. |
| 6,197,330 B1 | | 3/2001 | Rees et al. |
| 6,528,483 B1 | * | 3/2003 | Beaulieu et al. ................ 514/8 |

FOREIGN PATENT DOCUMENTS

| | | |
|---|---|---|
| CA | 2083741 A1 | 7/1993 |
| DE | 19905128 A1 | 8/2000 |
| EP | 0 179 477 A3 | 4/1986 |
| EP | 0179477 A | 4/1986 |
| EP | 0278103 A | 8/1988 |
| EP | 0 312 208 | 4/1989 |
| EP | 0 312 208 A1 | 4/1989 |
| EP | 0 407 008 A2 | 4/1989 |
| EP | 0 443 224 A1 | 8/1991 |
| EP | 0572272 A1 | 12/1993 |
| EP | 0572272 A1 * | 12/1993 |
| EP | 0 592 380 A1 | 4/1994 |
| EP | 0721355 B1 | 7/1996 |
| EP | 0901795 A2 | 3/1999 |
| EP | 0901795 A3 | 11/2000 |
| JP | 3232898 A | 10/1991 |
| JP | 5178897 A | 7/1993 |
| JP | 11-146909 A | 6/1999 |
| WO | WO 89/05653 | 6/1989 |
| WO | WO 90/06767 | 6/1990 |
| WO | WO 90/08833 | 8/1990 |
| WO | WO 90/13653 | 11/1990 |
| WO | WO 91/15233 | 10/1991 |
| WO | WO 92/12739 | 8/1992 |
| WO | WO 92/13003 | 8/1992 |
| WO | WO 93/08825 | 5/1993 |
| WO | WO 95/09658 A1 | 4/1995 |
| WO | WO 96/01658 A1 | 1/1996 |
| WO | WO 96/14453 A1 | 5/1996 |
| WO | WO 98/00180 A1 | 1/1998 |
| WO | WO 98/00446 A1 | 1/1998 |
| WO | WO 98/12228 A1 | 3/1998 |
| WO | WO98/26797 * | 6/1998 |
| WO | WO 99/27167 A1 | 6/1999 |
| WO | WO 00/55206 A1 | 9/2000 |

OTHER PUBLICATIONS

Smaglik, P. "Promise and Problems Loom for Stem Cell Gene Therapy," The Scientist (1999), p. 14, vol. 13, No. 15 and larger print version from The Scientist website.

Brown, C.D. et al., A Review of Topical Agents for Wounds and Methods of Wounding- Guidelines for Wound Management, Journal of Dermatology Surgery and Oncology, 1993, pp. 732-737, vol. 19.

"Carbopol® Resins -GC-67" BF Goodrich, 1990, Cleveland, OH.

Doran, J.E. et al., Cold Insoluble Globulin-Enhanced Phagocytosis of Gelatinized Targets by Macrophage Monolayers: A Model System, Journal of the Reticuloendothelial Society, 1980, pp. 471-483, vol. 27, No. 5.

Edwards, C.A. et al., "Tri (n-Butyl) Phosphate/Detergent Treatment of Licensed Therapeutic and Experiemental Blood Derivatives," Vox Sang. 1987, pp. 53-59, vol. 52.

Hynes, R. O., Fibronectins, 1990, Springer-Verlag.

Molnar, J et al., "Definition of Fibronectin-mediated Uptake of Gelatinized Latex by Liver Slices and Macrophages," Biochimica et Biophysica Acta, 1987, pp. 326-337, vol. 930.

Piet, M.P.J. et al., "The Use of Tri (N-butyl) phosphate Detergent Mixtures to Inactivate Hepatitis Viruses and Human Immunodeficiency Virus in Plasma and Plasma's Subsequent Fractionation," 1990, Transfusion, pp. 591-598, vol. 30., No. 7.

Radosevich, M., "Research and Development Commitments in an Integrated Plastma Collection and Plasma Factionation Environment," Seminars in Thrombosis and Hemostasis, 1998, pp. 157-161, vol. 24, No. 2.

Regnault, V. et al., "preparation de fibronectine humaine de haute purete fonctionnellement active," Revue Francaise de Transfusion et Immuno-hematologie, pp. 19-34, 1988, vol. 31, No. 1 (English Abstract).

Ruoslahti, E. et al., "Fibronectin Purification, Immunochemical Properties, and Biological Activities," Methods in Enzymology, 1982, pp. 803-831, vol. 82.

Harahap, M., "Differential Diagnosis of Leg Ulcers," Clinics in Dermatology, 1990, pp. 1-3, vol. 8, No. 3/4.

Harahap, M., "Leg Ulcers Caused by Bacterial Infections," Clinics in Dermatology, 1990, pp. 49-65, vol. 8, No. 3/4.

Phillips, T.J. et al., "Leg Ulcers," Journal of the American Academy of Dermatology, 1991, pp. 965-987, vol. 25, No. 6.

Eaglstein, W. H., "Effect of Occlusive Dressings on Wound Healing," Clinics in Dermatology, 1984, pp. 107-111, vol. 2, No. 3.

Eaglstein, W.H., "Current Wound Management: A Symposium," Current Wound Management, 1984, pp. 134-142, vol. 2, No. 3.

Eaglstein, W.H. et al., "Effect of Topically Applied Agents on Healing Wounds," Clinics in Deramtology, 1984, pp. 112-115, vol. 2, No. 3.

Mulder, G.D., "Clinical Protocols for Studying Wound Healing," Clinical Materials, 1991, pp. 251-255, vol. 8.

Siner, A. J. et al., "Cutaneous Wound Healing," New England Journal of Medicine, 1999, pp. 738-746, vol. 341, No. 10.

Clark, R. A. F., "Potential Roles of Fibronectin in Cutaneous Wound Repair," Arch. Deramtol., 1986, pp. 201-206, vol. 124.

Norris, D. A. et al., "Fibornectin Fragment(s) are Chemotactic for Human Peripheral Blood Monocytes," Journal of Immunology, 1982, pp. 1612-1618, vol. 129, No. 4.

Clark, R. A. F., "Cryptic Chemotactic Activity of Fibronectin for Human Monocytes Resides in the 120-kDA Fibroblastic Cell-binding Fragment," Journal of Biological Chemistry, 1988, pp. 12115-12123, vol. 263, No. 24.

Ali, I. U. et al., "Effects of LETS Glycoprotein in Cell Motility," Cell, 1978, pp. 439-446, vol. 14.

Postlethwaite, A. E. et al., "Induction of Fibroblast Chemotaxis by Fibronectin: Localization of the Chemotactic Region to a 140,000-Molecular Weight Non-Gelatin-binding Fragment," J. Exp. Med., 1981, pp. 494-499, vol. 153.

Seppa, H. E. J. et al., "The Cell Binding Fragment of Fibronectin is Chemotactic for Fibroblasts," Cell Biology International Reports, 1981, pp. 813-819, vol. 5, No. 8.

Bowersox, J. C. et al., "Chemotaxis of Aortic Endothelial Cells in Response to Fibronectin," Cancer Research, 1982, pp. 2547-2551, vol. 42.

O'Keefe, E. J. et al., "Production of Soluble and Cell-Associated Fibronectin by Cultured Keratinocytes,"Journal of Investigative Dermatology, 1984, pp. 150-155, vol. 82, No. 2.

Mosesson, M. W. et al., "The Cold-insoluble Globulin of Human Plasma," Journal of Biological Chemistry, 1970, pp. 5728-5736, vol. 245, No. 21.

Weiss, E. et al., "Un-Cross-Linked Fibrin Substrates Inhibit Keratinocyte Spreading and Replication: Correction with Fibronectin and Factor XIII Cross-Linking," Journal of Cellular Physiology, 1998, pp. 58-65, vol. 174.

Czop, J. K., "Phagocytosis of Particulate Activators of the Alternative Complement Pathway: Effects of Fibronectin," Advances in Immunology, 1986, pp. 361-398, vol. 38.

Bevilacqua, M. P. et al., "Receptors for Cold-Insoluble Globulin (Plasma Fibronectin) on Human Monocytes," J. Exp. Medicine, 1981, pp. 42-60, vol. 153.

Pommier, C. G. et al., "Plasma Fibronectin Enhances Phagocytosis of Opsonized Particles by Human Peripheral Blood Monocytes," J. Exp. Medicine, 1983, pp. 1844-1854, vol. 157.

Brown, E. J., "The Role of Extracellular Matrix Proteins in the Control of Phagocytosis," Journal of Leukocyte Biology, 1988, pp. 579-591, vol. 39.

Grinnell, F. et al., "Initial Adhesion of Human Fibroblasts in Serum-Free Medium: Possible Role of Secreted Fibronectin," Cell, 1979, pp. 117-129, vol. 17.

Takashima, A. et al., "Fibronectin-Mediated Keratinocyte Migration and Initiation of Fibronectin Receptor Function in Vitro," Journal of Investigative Dermatology, 1985, pp. 304-308, vol. 85.

Clark, R. A. F. et al., "Fibronectin, as Well as Other Extracellular Matrix Proteins, Mediate Human Keratinocyte Adherence," Journal of Investigative Dermatology, 1985, pp. 378-383, vol. 84.

O'Keefe, E. J. et al., "Spreading and Enhancing Motility of Human Keratinocytes on Fibronectin," Journal of Investigative Dermatology, 1985, pp. 125-130, vol. 85.

Macarak, E. J. et al., "Adhesion of Endothelial Cells to Extracellular Matrix Protein," Journal of Cellular Phsiology, 1983, pp. 76-88, vol. 116.

Palotie, A. et al., "Components of Subendothelial Aorta Basement Membrane," Laboratory Investigation, 1983, pp. 382-370, vol. 49, No. 3.

Clark, R. A. F. et al., "Either Exogenous or Endogenous Fibronectin Can Promote Adherence of Human Endothelial Cells," J. Cell. Sci., 1986, p. 263-280, vol. 82.

Horsburgh, C. R. et al., "Lymphokines and Platelets Promote Human Monocyte Adherence to Fibrinogen and Fibronectin in Vitro," Journal of Leukocyte Biology, 1987, pp. 14-24, vol. 41.

Grinnell, F. et al., "Distribution of Fibronectin During Wound Healing in Vivo," The Journal of Investigative Dermatology, 1981, pp. 161-189, vol. 76, No 3.

Repesh, L A. et al., "Fibronectin Involvement in Granulation Tissue and Wound Healing in Rabbits," The Journal of Histochemistry and Cytochemistry, 1982, pp. 351-358, vol. 30, No. 4.

Clark, R. A. F. et al., "Fibronectin and Fibrin Provide a Provisional Matrix for Epidermal Cell Migration During Wound Reepithelialization," The Journal of Investigative Dermatology, 1982, pp. 264-269, vol. 79, No. 5.

Clark, R. A. F. et al., "Blood Vessel Fibronectin Increases in Conjuction with Endothelial Cell Proliferation and Capilarry Ingrowth During Wound Healing," The Journal of Investigative Deramtology, 1982, pp. 269-276, vol. 79, No. 9.

Hedman, K. et al., "Isolation of the Pericellular Matrix of Human Fibroblast Cultures," J. Cell Biology, 1979, pp. 83-91, vol. 81.

Hedman, K. et al., "Strucutre of the Pericellular Matrix: Association of Heparan and Chondroltin Sulfates with Fibronectin-Procollagen Fibers," Cell, 1982, pp. 663-671, vol. 28.

Hedman, K. et al., "Integrity of the Pericellular Fibronectin Matrix of Fibroblasts is Independent of Sulfated Glycosaminoglycans," The EMBO Journal, 1984, pp. 581-584, vol. 3, No. 3.

Carter, W. G., "The Role of Intermolecular Disulfide Bonding in Deposition of GP140 in the Extracellular Matrix," Journal of Cell Biology, 1984, pp. 105-114, vol. 99.

Clark, R. et al., "TGF-β1 Stimulates Cultured Human Fibroblasts to Proliferate and Produce Tissue-Like Fibroplasts: A Fibronectin Matrix-Dependent Event," Journal of Cellular Physiology, 1997, pp. 69-80, vol. 170.

Nakada, M. et al., "Efficacy of Exogenous Fibronectin in Wound Healing in Malnourished Rats," Journal of Pediatric Surgery, 1998, pp. 1699-1702, vol. 33, No. 11.

Cheng, C.Y. et al., "Fibronectin Enhances Healing of Excised Wounds in Rats," Arch. Dermatol., 1988, pp. 221-225, vol. 124.

Kono, I. et al., "Beneficial Effect of Topical Fibronectin in Patients with Keratoconjunctivitis Sicca of Sjogren's Syndrome," Journal of Rheumatology, 1985, pp. 487-489, vol. 12.

Nishida, T. et al., "Fibronectin Enhancement of Comeal Epithelial Wound Healing of Rabbits In Vivo," Arch. Opthalmol., 1984, pp. 455-456, vol. 102.

White, H., "A Heteroskedasticity-Consistent Covariance Matrix Estimator and a Direct Test for Heteroskedasticity," Econometrica, 1980, pp. 817-838 vol. 48, Issue 4.

Collett, D,, "Model Checking in the Proportional Hazards Model," Chapter 5 in Modelling Survival Data in Medical Research, 1994, 1st edition, Chapman & Hall, London; New York.

Katz, M.H. et al., "Proportional Hazards (Cox) Regression," Journal of General Internal Medicine, 1993, pp. 702-711, vol. 8.

Schemper, M., "Cox Analysis of Survival data with Non-Proportional Hazard Functions," Statistician, 1992, pp. 455-465, vol. 41, Issue 4.

Greenland, S., "Modeling and Variable Selection in Epidemiologic Analysis," American Journal of Public Health, 1989, pp. 340-349, vol. 79, No. 3.

Robins, J. M. et al., "The Role of Model Selection in Causal Inference from Nonexperimental Data," American Journal of Epidemiology, 1986, pp. 392-402, vol. 123, No. 3.

Falanga, V., "Care of Venous Leg Ulcers," Ostomy/Wound Management, 1999, pp. 33S-43S, vol. 45 (Suppl. 1A).

Margolis, D. et al., "Risk Factors Associated with the Failure of a Venous Leg Ulcer to Heal," Arch. Dermatol., 1999, pp. 920-926, vol. 135.

Marston, W. A. et al., "Healing Rates and Cost Efficacy of Outpatient Compression Treatment for Leg Ulcers Associated with Venous Insufficiency," J. Vasc. Surgery, 1999, pp. 491-498, vol. 30, No. 3.

Olin, J. W. et al., "Medical Costs of Treating Venous Stasis Ulcers; Evidence from a Retropsective Cohort Study," Vascular Medicine, 1999, pp. 1-7, vol. 4.

Phan, T.-M. M. et al., "Topical Fibronectin in the Treatment of Persistent Comeal Epithelial Defects and Trophic Ulcers," American Journal of Opthalmology, 1987, pp. 494-501, vol. 104.

Fleiss, J., Statistical Methods for Rates and Proportions, 1981, pp. 38-42, John Wiley and Sons, New York.

Lachin, J. M. et al., "Evaluation of Sample Size and Power for Analyses of Survival with Allowance for Nonuniform Patient Entry, Losses to Follow-Up, Noncompliance, and Stratificiation," Biometrics, 1988, pp. 507-519, vol. 42, Issue 3.

Hosmer, D. et al., Applied Logistic Regression, 1989, pp. 149-170, John Wiley and Sons, New York.

Devlin, TM. Textbook of Biochemistry: with Clinical Correlations. Wiley: New York, 1997. pp. 5-7, 9, 34-37.

Harper, HA. Harper's Biochemistry. Appleton & Lange: Norwalk, Connecticut, 1988.

Hynes, RO. Fibronectins. Springer-Verlag: New York, 1990. pp. 12-14.

Lehninger, AL. Cox, MM. Nelson, DL. Principles of Biochemistry. Worth Publishers: New York, 1993, pp. 137-143, 745.

Meyers, RA. Encyclopedia of moelcular biology and moelcular medicine. VCH Publishers: Weinheim, New York, 1996-1997. pp. 282-283.

Stryer, L. Biochemistry. W.H. Freeman: New York, 1995.

Van Holde, KE. Johnson, WC. Ho, PS. Principles of Biochemistry. Prentice Hall: Upper Saddle River, New Jersey, 1998. pp. 16-17.

Voet, D., Voet, Judith G. Biochemistry John Wiley & Sons, Inc. 1995. pp. 72-77.

Horowitz, B., Chang, MY. Preparation of Fibronectin for Therapeutic Administration in Mosher, Of Fibronectin. Academic Press: San Diego, 1989. pp. 441-455.

Sibbald, RG. Ostomy/Wound Management 44(9). 1998. pp. 52-58, 60-66.

Draget, Kurt I. et al., "Alginate based new materials," International Journal of Biological Macromoleucles, 1997, vol. 21, pp. 47-55, Elsevier Science B.V.

Piacquadio, D. et al., "Alginates," J. Dermatol. Surg. Oncol. 1992 18:990-98, Elsevier Science Publishing Co., Inc.

Moe, S. et al., "Calcuim Alginate Gel Fibers: Influence of Alginate Source and Gel Structure on Fiber Strength," Journal of Applied Polymer Science, 51:1771-75 (1994), John Wiley & Sons, Inc.

Pronova Biopolymer, "Dermatology and Wound Healing, Histroy and clinical use of Alginate, . . ."(Date of at least Jan. 30, 1998) Prescott Canada World Chemical Distributors, Toronto and Montreal.

Potts, J.R. et al., "Fibronectin structure and assembly," Current Opinion in Cell Biology (1994) 6:648-552.

Gehrke, S.H. et al.., "Hydrogels for Drug Delivery Systems," In Specialized Drug Delivery Systems Manufacturing and Production Technology, Chapter 8, (1990) vol. 41, pp. 333-392, Marcel Dekker, New York.

Mustoe, T.A. et al., "Growth Factor-induced Acceleration of Tissue Repair through Direct and Inductive Activities in a Rabbit Dermal Ulcer Model," J. Clin Invest (1991) 87:694-703.

Kornblihtt et al., EMBO J. (1985) 4:1755-1759.

Bradford, M., "A Rapid and Sensitive Method for the Quantitation of Microgram Quantities of Protein Utilizing the Principle of Protein-Dye Binding," Anal. Biochem. (1976) 72:248-254.

Radosevich, M., "Research and Development Commitments in an Integrated Plasma Collection and Plasma Fractionation Environment," Seminars in Thrombosis and Hemostasis. (1998) 24 (2) 157-161.

Horowitz, B. et al., "Solvent/Detergent-Treated Plastma; A Virus-Inactivated Substitute for Fresh Frozen Plasma," Blood (1992) 79 (3):826-31.

Boisjoly, H.M. "Topical Fibronectin and Aprotinin for Keratectomy Wound Healing in Rabbits," Arch. Opththalmol. 108:1758-63 (1990).

Hynes, R.O., Methods for identification of fibronectin (chap 2., p. 12) In: Fibronectins New York: Springer-Verlag 1990.

Hynes, R.O., Methods for identification of fibronectin (chap. 2, pp. 7-23) and Wound healing, inflammation, and fibrosis (chap. 14, pp. 349-364, in: Fibronectins New York: Springer-Verlag, 1990.

Brotchie, H., Wakefield, D. Fibronectin: Structure, function and significance in wound healing. Australas J. Dermatol 1990; 11:47-56.

Nishida, T. et al., Rapid Preparation of Purified Autologous Fibronectin Eyedrops, Jpn. J. Opthalmol (1982) 26:416-24.

Phan, T. H. et al., Topical Fibronectin in the Treatment of Persistent Corneal Epithelial Defects and Trophic Ulcers, Am. J. Opthalmol (1987) 104:494-501.

Wysocki, A. et al., Topical Fibronectin Therapy for Treatment of a Patient With Chronic Stasis Ulcers, Arch Dermatol (1988) 124:175-77.

Edwards, C.A. et al., Tri (n-butyl) Phosphate/Detergent Treated of Licensed Therapeutic and Experimental Blood Derivatives, Vox Seng (1987) 52:53-59.

Horowitz, B. et al., Solvent/Detergent-Treated Plasma: A Virus-Inactivated Substitute for Fresh Frozen Palsma, Blood (1992) 79:826-31.

Grinnell, F. et al., Degradation of Fibronectin and Vitronentin in Chronic Wound Fluid: Analysis by Cell Blotting, Immunoblotting and Cell Adhesion Assays, J Invest Dermatol (1992) 98:410-416.

Chen, W.Y.J. et al., Characterization of Biologic Properties of Wound Fluid Collected During Early Stages of Wound Healing, J Invest Dermatol (1992) 99:559-64.

berman, H. et al., Ulceration is Correlated With Degradation of Fibrin and Fibronectin at the Corneal Surface, Invest Ohpthalmol Vis Sci (1983) 24:1358-66.

Horowitz, N. et al., Preparation of Fibronectin for Therapeutic Administration, In: O.F. Mosher (ed.), Fibronectin, pp. 441-55, San Diego, Academic Press (1989).

Franz, T.J., Percutaneous Absortion. On the Relevance of In Vitro Data, J Invest Dermatol (1975) 64:190-95.

Bronaugh, R.L. et al., Methods for In Vitro Percutaneous Absorption Studies I: Comparison with In Vivo Results, Toxicol Appl Pharmacol (1982) 62:474-80.

Bronaugh, R.L. et al., Methods for In Vitro Percutaneous Absorption Studies IV: The Flow-Through Diffusion Cell, J Pharm Sci (1985) 74:64-67.

Saba, T.M. et al., "Prevention of Liver Reticuloendothelial Systemic Host Failure After Surgery by Intravenous Opsonic Glycoprotein Therapy," *Annals of Surgery*, 188:142-52 (1978).

Scovill, W.A. et al., "Opsonic $\alpha_2$ Surface Binding Glycoprotein Therapy During Sepsis," *Annals of Surgery*, 188:521-29 (1978).

Yamada, K.M. et al., "Fibronectins—Adehsive Glycoproteins of Cell Surface and Blood," *Nature*, 275:179-84 (1978).

Denaturing (SDS) Discontinuous Gel Electrophoresis: Laemmli Gel Method, pp. 10.2.4-10.2.9, Current Protocols in Molecular Biology (1994).

Pharmaceuticals and Specialities Compendium, p. 1215, Canadian Pharmaceutical Assn. (1995).

* cited by examiner

US 7,112,320 B1

SOLID WOUND HEALING FORMULATIONS CONTAINING FIBRONECTIN

RELATED APPLICATIONS

This application is the United States national phase application of International Application No. PCT/CA00/00953 filed Aug. 21, 2000. International Application No. PCT/CA00/00953 claims the priority of both U.S. Provisional Application No. 60/149,958 filed Aug. 20, 1999 and U.S. Provisional Application No. 60/182,412 filed Feb. 14, 2000.

This application is also a continuation-in-part U.S. application Ser. No. 09/331,344, filed Aug. 21, 1999 (completion of 371 requirements), which is the United States national phase application of International Application No. PCT/CA97/00966, filed Dec. 12, 1997, which claims the priority of U.S. application Ser. No. 08/767,868, filed Dec. 17, 1996, which issued as U.S. Pat. No. 5,821,220. U.S. application Ser. No. 08/767,868 is a continuation-in-part of U.S. application Ser. No. 08/488,253, filed Jun. 7, 1995, which issued as U.S. Pat. No. 5,641,483.

This application is also a continuation-in-part of U.S. application Ser. No. 09/862,971, filed May 22, 2001, which is a divisional application of U.S. application Ser. No. 09/245,785, filed Feb. 5, 1999, which is a divisional application of U.S. application Ser. No. 08/879,159, filed Jun. 19, 1997, which issued as U.S. Pat. No. 5,877,149. U.S. application Ser. No. 08/879,159 is a continuation-in-part of U.S. application Ser. No. 08/488,253, filed Jun. 7, 1995, which issued as U.S. Pat. No. 5,641,483.

FIELD OF THE INVENTION

The present invention relates to solid wound dressings which release effective amounts of fibronectin, in particular fibronectin-calcium alginate dressings.

BACKGROUND OF THE INVENTION

Fibronectin is a ubiquitous extracellular glycoprotein containing around 5% carbohydrate. It exists in a soluble form in body fluids and in an insoluble form in the extracellular matrix. Fibronectin plays a major role in many important physiological processes, such as embryogenesis, hemostasis, thrombosis and wound healing (Potts, J. R. and Campbell, I. D. Current Opinion in Cell Biology 6:648–55, 1994). The characteristic form of plasma fibronectin is a disulfide-bonded dimer of 440,000 daltons, each subunit having a molecular weight of about 220,000 daltons. Plasma fibronectin is also known by various other names, including cold-insoluble globulin, antigelatin factor, cell attachment protein, cell spreading factor, and opsonic alpha 2-surface binding glycoprotein. These names reflect biological activities of fibronectin such as cell recruitment, opsonization of particulate debris, and promotion of wound contraction. Reviews on structure and activities of fibronectin have been published elsewhere (Hynes, R. O. *Fibronectins*, Rich, A., ed. New York, Springer-Verlag 1990).

Wound healing is usually divided into three phases: the inflammatory phase, the proliferative phase, and the remodeling phase. Fibronectin has been reported to be involved in each stage of the wound healing process, particularly by creating a scaffold to which the invading cells can adhere. Initially, there is a release of many mediators to the wound site such as fibronectin and fibrinogen. Fibronectin promotes inflammatory cell migration into the wound and debris phagocytosis by monocytes. Thereafter, angiogenesis and reepithelialization take place. At this stage, fibronectin exerts chemotactic activity on endothelial cells, and promotes epithelial cell and fibroblast migration onto the basal membrane. Fibronectin also appears to be an essential component of the remodeling phase where it plays a major role in the organization of collagen fibrils. The fibrillar collagen ultimately forms fibrous bundles that greatly enhance the tissue tensile strength, leading to wound closure. Normally found in plasma at a concentration of about 300 µg/mL, fibronectin is extracted and purified using a method developed by Horowitz and Chang (Horowitz, B. and Chang, M. D. Y. "Preparation of fibronectin for therapeutic administration in *Fibronectin*, D. F. Mosher ed., Academic Press, San Diego 441–455 (1989)).

Topically applied plasma fibronectin has been reported as being useful for increasing the rate of wound healing such as in corneal wounds (Nishida, T. et al., Japan Journal of Ophthalmology 26: 416–24, 1982; Phan, T. M. et al., American Journal of Ophthalmology 104:494–501, 1987) and leg ulcers (Wysocki, A. et al., Arch. Dermatology 124: 175–177, 1988). However, there is no suitable topical carrier for use in treating wounds that can ensure delivery of an effective amount of fibronectin in a pharmaceutically acceptable formulation. A major limiting factor in developing an effective topical dosage form of a drug is not only having an active drug, but also having a formulation that allows the passage of the active drug from the carrier into a site of delivery.

A topical formulation, which maximizes the contact time of fibronectin to the wound and controls the release of fibronectin into the wound, is a hydrogel formulation. In drug delivery, the term hydrogel is typically reserved for polymeric materials that can absorb a significant amount of water (>20% of its dry weight) while maintaining a distinct three-dimensional structure (Gehrke, S. H. and Lee, P. I., "Hydrogels for drug delivery systems," In *Specialized Drug Delivery Systems Manufacturing and Production Technology*, Chapter 8, Vol. 8, PP 333–392, Marcel Dekker, New York 1990). The most important characteristic of a hydrogel is its degree of swelling in water. Hydrogels mimic living tissue more closely than any other non-natural material. Their immediate resemblance to tissue is in their soft, flexible nature and high water content. This helps minimize mechanical irritation and damage to body tissues. Other advantages of hydrogel formulations include: ability to keep the wound moist which results from their high water content, ability to absorb excess water (exudate) in the wound, ease of application to and removal (by washing) from the wound. They also provide a cool feeling when topically applied, a property that can increase patient comfort.

Hydrogels have four major properties: swelling degree, biocompatibility, permeability and swelling kinetics. Example of such compounds include vinyl polymers (e.g. polyacrylic acid), cellulose and cellulose derivatives. Polyacrylic acid polymer, also referred to as carbomer, e.g. Carbopol® carbomer (BF Goodrich), was chosen over other polymers (e.g. cellulose and cellulose derivatives), because it was shown to be superior to other pharmaceutically acceptable formulations in the delivery of fibronectin to skin wounds.

Hydrogel formulations comprising a water soluble, pharmaceutically acceptable polymer which can include increasing concentrations of fibronectin are described in U.S. Pat. No. 5,641,483, entitled "Wound Healing Formulations containing Human Plasma Fibronectin", which is incorporated by reference herein in its entirety. Methods for preparing non-buffered aqueous concentrated solutions of fibronectin and hydrogels containing up to 1% of fibronectin are described in U.S. Pat. No. 5,821,220, entitled "Method of Producing Concentrated Non-Buffered Solutions of Fibronectin" and International Application No. PCT/CA97/00966, International Publication No. WO 98/26797, entitled "Wound Healing Formulations Containing Human Plasma Fibronectin", both of which are incorporated herein by reference in their entirety.

Alginates are naturally occurring substances extracted from marine brown algae and used in the pharmaceutical, cosmetic, textile and food industry. Alginates are polyanionic polysaccharides composed of linear binary copolymers of D-mannuronic acid and L-guluronic acid. The most common uses are based on the polyelectrolytic nature of the alginates, which provides the basis of their gelling properties and their ability to swell. The commercially available sodium alginates are water soluble. When such alginates are added to a solution containing polyvalent ions, for example bivalent alkaline earth metal ions such as $Ca^{++}$, alginate gels having a semi-solid form are produced. This is a result of a ionic crosslinking of several alginate chains.

Calcium alginates have long been known for their ability to form fibres or nonwoven materials. These have been used primarily as swabs or dressings for medical, surgical or other purposes, such as described in European Patent Specification, EP 0721355 B1, entitled "Alginate Wound Dressings, which is incorporated herein by reference in its entirety. Supplied in the form of nonwoven wound dressings for the treatment of exudating wounds, the calcium alginate dressing is said to encourage the formation of controlled ion-active gel over the wound site which reacts with the sodium ions in the exudate. Examples of exudative wounds include pressure ulcers, venous stasis ulcers, diabetic ulcers, arterial ulcers, second degree burns and skin graft donor sites.

SUMMARY OF THE INVENTION

The present invention provides techniques for the creation of solid wound dressings capable of delivering an effective wound healing amount of fibronectin to a wound site. Examples of solid dressings used to deliver the fibronectin are based on calcium alginate, carboxymethylcellulose (CMC), hydroxypropylcellulose (HPC), carbomer and carrageenan.

Formulation of topical dosage forms intended for the incorporation of fibronectin should respect several quality criteria. All components of the preparation including solvents and gelling agents should be nontoxic for the wound and compatible with the drug. The final product should promote optimal release of the drug to its site of action, be of adequate consistency to enhance contact time of the drug with the wound and be sterile.

Use of solid dressings of the present invention offer specific advantages in terms of dose reproducibility, ease of storage, transport and application. In addition, preservatives are not needed.

These solid dressings provide a slow release of fibronectin to the delivery site. This should allow for the application of the solid wound dressings on a convenient once a day basis. Due to once a day application schedule and their solid form, the trauma done to the wound by the removal of depleted doses should be minimized.

The preferred formulations of this invention can be used with other wound healing promoters having a composition similar to fibronectin, such as proteins of similar size (thrombospondin, laminin, vitronectin, fibrinogen) or smaller size (such as peptides including growth factors).

The preferred formulations can be evaluated using an in vitro diffusion cell system consisting of a rigid receptor containing a deepithelialized skin sample, the deepithelialized side facing upwards into a donor compartment and the dermal side facing downwards into a receptor compartment as described in detail in U.S. Pat. No. 5,877,149, entitled "Deepithelialized Skin Diffusion Cell System," which is incorporated herein by reference. The receptor compartment is connected to a circulating buffer circuit, with the buffer temperature maintained at 37° C., while the skin surface is about 32° C.

DETAILED DESCRIPTION OF THE INVENTION

Example 1

Solid Fibronectin Calcium-Alginate Wound Dressing Formulation

Figure 1:
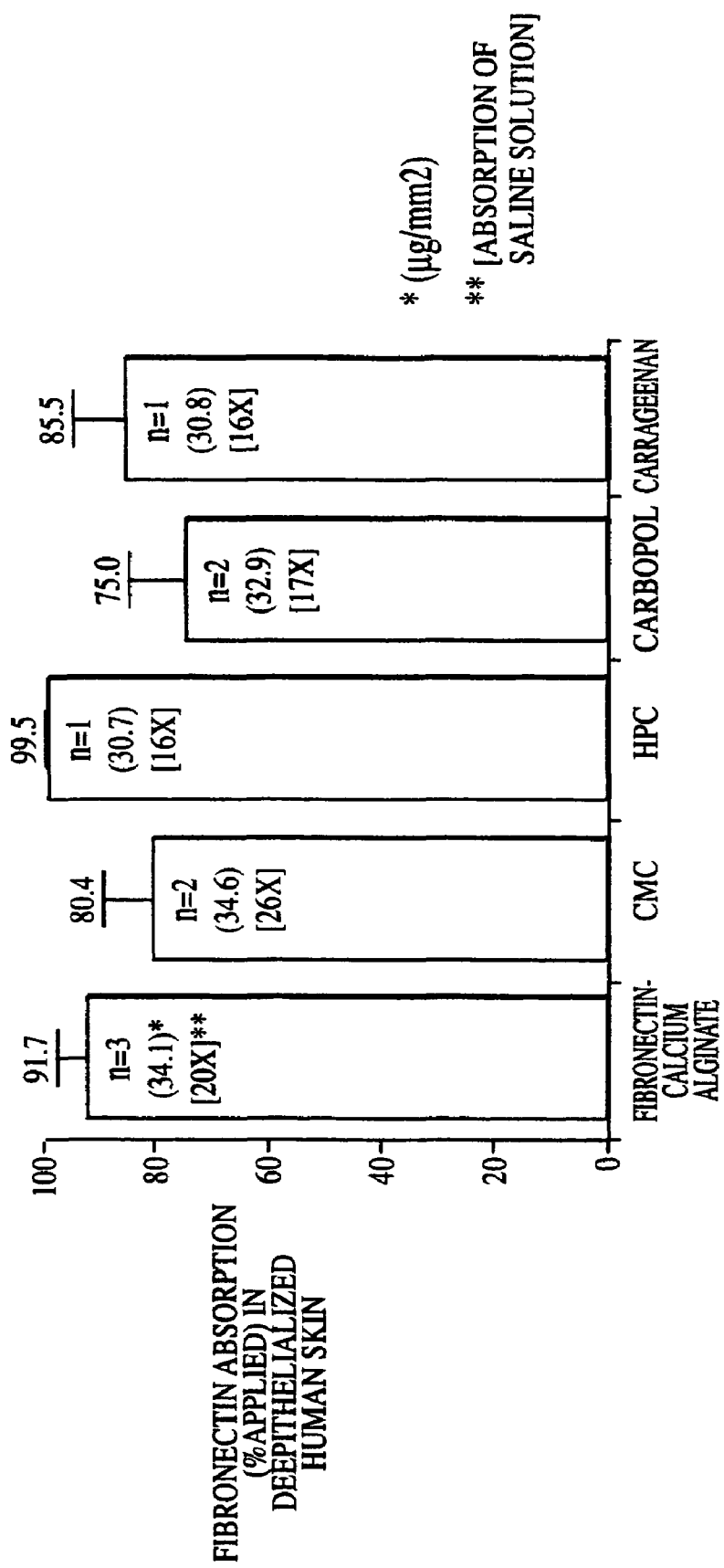
FIG. 1 shows absorption of fibronectin in deepithelialized human skin using different solid wound dressings over a 24 hour period. The number in ( ) refers to the quantity of absorbed fibronectin (μg) per $mm^2$ of deepithelialized human skin over a 24 hour period. The number in [] refers to the quantity of absorbed saline solution (0.9% NaCl) by weight of dressing. Bars represent standard deviations of the mean.

Alginate salts, as well as the dressing systems described in subsequent examples, can be converted into fibers by a process of freeze-drying. This procedure produces a sponge-like structures with hydrophilic properties. In the presence of fluids, the dressings turn into a gel-like state, capable of absorbing up to 20 times their weight in wound exudate. The fibrous gel thereby creates the desired moist environment for the wound. The dressings can also be removed with a minimal amount of discomfort, minimizes the formation of granulation tissue and does not traumatize epithelial cells during dressing changes.

The fibronectin-calcium alginate and other fibronectin solid wound dressings according to the invention can store fibronectin without degradation for long periods of time, at least 12 months at 4° C. The residual moisture in these dressing is low, around 5%.

The fibronectin-calcium alginate and other fibronectin-solid wound dressings according to the invention deliver a high concentration of fibronectin into the wound site.

The basic mechanisms at play for the fibronectin-calcium alginate dressing is that when this dressing comes into contact with the sodium in the exudate, ion exchange occurs, turning the calcium alginate fibers into a protective non-adherent film gel. In this gel state, fibronectin is free to move from the gel into the wound.

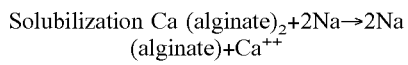

Solubilization Ca (alginate)$_2$+2Na→2Na (alginate)+Ca$^{++}$ $Ca^{++}$ forms an insoluble alginate salt and $Na^+$ forms a soluble alginate salt (the equivalent ratio of the first to second cations being 50:50, here 0.2M NaCl and 0.2MCaCl$_2$). The maximum homogeneity in the dressing is reached by an appropriate concentration of both gelling and non-gelling cations. Additional Na+ comes from the exudate or, if the wound is too dry or there is no exudate, a small amount of saline can be added to the wound immediately prior to placing the dressing.

Because alginates are anionic polysaccharides, the complex is preferably formed by combining the fibronectin and sodium alginate at a pH which is no higher than the isoelectric point of the protein (pI 6.2) where the fibronectin is positively charged. This pH is achieved by adding glacial acetic acid for a final pH around 5.0. Since acetic acid is highly volatile, a certain amount of acetic acid is removed during the freeze-drying process which is under a vacuum. The final pH of the dressing is around 6.5.

The mixed salt alginate dressing exhibits a highly effective combination of properties. For example, there is enough insolubilizing cation in the mixed salt alginate to make the product relatively easy to manipulate. There is also enough solubilizing cation to facilitate the release of fibronectin into the wound. The combination of soluble and insoluble alginate fibers has the further advantage that the dressing is both easily removed after the wound treatment and easily applied initially.

Fibronectin-Calcium Alginate Dressing Composition

Three commercially available preparations of sodium alginate were tested. Protanal LF 120 M sodium alginate (Pronova Biopolymer, Inc., Drammen, Norway) yielded a product more brittle than the preferred embodiment described below. In addition, this sodium alginate yielded a placebo dressing (i.e., control without fibronectin) which was yellowish in appearance compared to the same dressing containing fibronectin. Consequently, this formulation could not be used in human clinical trials. A particularly preferred alginate is Pronova UP LVG sodium alginate (Pronova Biomedical A.S., Oslo, Norway).

In one embodiment of the present invention, the fibronectin-calcium alginate wound dressing is prepared as follows: 5 g of sodium alginate (Protanal LF 10/60, Pronova Biopolymer, Drammen, Norway) are dispersed in 95 g of deionized and demineralized water with a paddle type stirrer for about 1 hour. The colloidal dispersion thus produced provides a concentrated sodium alginate base (5% w/w), which is then autoclaved. The pH of a sterile filtered 1% solution of sodium alginate prepared from this concentrate is adjusted to 4.0 using acetic acid (3.33 µL of glacial acetic 17.4N in 100 Ml of demineralized water provides a pH of 4.0). Tap water is demineralized using a Millipore Milli-Q water system. The terms demineralized and deionized are used interchangeably throughout this application. The pH of 10 mL demineralized water is adjusted to pH 8.0 to 11.0 as described in Example 9. In the following preferred embodiment, the pH is adjusted to 11.6.

0.025 to 0.1 g, preferably 0.1 g, of lyophilized human plasma fibronectin, prepared according to Example 10, is next dissolved in demineralized water, pH 11.6. The solution is maintained at 37° C. until the fibronectin is completely dissolved. The fibronectin solution is then filtered through a 0.22 µm acetate filter. This solution constitutes the stock fibronectin solution used in this and subsequent examples.

3.4 ml of the resulting 0.25% to 1% sterile solution of fibronectin is then mixed with 1.5 mL of the pH adjusted, dilute sodium alginate solution described above. The sterile fibronectin and sterile sodium alginate solutions are mixed into syringes taking care to avoid the introduction of air bubbles. Contamination is avoided by working in an aseptic environment, such as under a laminar flow hood. Generally, two syringes are used, and multiple exchanges under pressure are applied. An adapter device, such as a female luer connection can be used to connect the syringes or other exchange devices. Vigorous agitation is minimized in order to avoid fibronectin precipitation.

Gellation of the solution is achieved by the addition of 15 μL 0.2 M NaCl+0.2 M $CaCl_2$ and 3.4 μL of glacial acetic acid. At this point, the fibronectin-calcium alginate complex is deposited in a borosilicate glass vial (5 mL for a surface area of 5.3 $cm^2$) and frozen at −20° C. for 2 hours and 30 minutes at −80° C. A preferred vial is 22.5 mm in width, 46.5 mm in height with an aluminum seal (part no. 24-0396, Comar, Buena, N.J.). The water is then removed by freeze-drying using a Labconco freeze-dryer (model 77580, Kansas City, Mo.). By this technique, a solid sponge-like fibronectin-calcium alginate wound dressing is produced, which has a surface area of 4.2 $cm^2$ and a fibronectin concentration up to 80 $μg/mm^2$. It should be noted that solid wound dressings could also be prepared with other insoluble fibers. They could be any insoluble fibers or materials which does not have adverse effect on the wound. Examples of suitable plant polysaccharides are carrageenans and cellulose derivatives for instance carboxymethylcellulose or hydroxypropylcellulose are described in the following examples. An embodiment using a synthetic carbomer resin is also illustrated. Tissue matrices and artificial skin systems, for example, as described in U.S. Pat. No. 4,963,489, entitled "Three-Dimensional Cell and Tissue Culture system, incorporated by reference, can also be employed in embodiments of the present invention.

Example 2

Solid Carboxymethylcellulose (CMC) Dressing

A preferred grade is GPR® CMC (BDH Laboratories, Ville St-Laurent, Canada). A solid wound dressing containing (w/w) fibronectin 62%, CMC 38% was prepared as follows. CMC powder was first sterilized by using a dry-heat sterilization process at 121° C. for 30 minutes using an American Sterilizer 2020 Vacamtic Eagle series autoclave (Steris Corp., Ohio). 6 grams of CMC were dispersed in 94 mL of demineralized water and mixed with a paddle type stirrer for about 3 hours. This provides a sterile concentrated hydrogel base (6% w/w).

Separately, 50 mg of lyophilized human plasma fibronectin, prepared according to Example 10, was dissolved in deionized water (5 mL) containing 12 μL of NaOH 3M, for a final pH of 11.6. The solution was maintained at 37° C. until the complete solubilization of fibronectin occurred. This stock solution of fibronectin 10 mg/mL was filtered through a 0.22 μm acetate filter. 3.3 mL of this fibronectin solution was then added to 0.34 g of the concentrated CMC base and mixed with syringes as described in Example 1. The pH is adjusted to 7.0 with the addition of 25 μL HCl 1N. At this point, the homogenous solution of the fibronectin-CMC complex was deposited in a plastic mold and frozen. A Costar 6-well polystyrene cell culture cluster, 9.6 $cm^2$ rounded surface area (Corning Inc., Corning, N.Y.) was used as the plastic mold. The water is then removed by freeze-drying using a Labconco freeze-dryer (model 77580, Kansas City, Mo.). By this technique, a fibronectin-CMC wound dressing with a sponge-like structure is produced.

Example 3

Solid Hydroxypropylcellulose (HPC) Dressing

Solid hydroxypropylcellulose (HPC) dressing was prepared using the preferred grade of Klucel-HF® HPC (Aqualon, Houston, Tex.). A solid wound dressing containing (w/w) fibronectin 45%, HPC 55% was prepared as follows. HPC powder was first sterilized by using a dry-heat sterilization process at 121° C. for 30 minutes using an American Sterilizer 2020 Vacamtic Eagle series autoclave (Steris Corp., Ohio). HPC (6 g) was then dispersed in 94 mL of deionized water and mixed with a paddle type stirrer for about 3 hours. This provides a sterile, concentrated hydrogel base (6% w/w). Separately, 50 mg of lyophilized human plasma fibronectin, prepared according to Example 10, were dissolved in 5 mL of deionized water containing 12 μL of NaOH 3M, pH 11.6. The solution was maintained at 37° C. until complete solubilization of fibronectin occurred. This stock solution of fibronectin, 10 mg/mL, was filtered through a 0.22 μm acetate filter. 3.3 mL of the fibronectin solution was then added to 0.68 g of concentrated HPC base and mixed with syringes as described in Example 1. The pH is adjusted to 7.0 with the addition of 25 μL HCl 1 N. At this point, the homogenous solution of the fibronectin-HPC complex is deposited in a plastic mold and frozen. A Costar 6-well polystyrene cell culture cluster, 9.6 $cm^2$ rounded surface area (Corning Inc., Corning, N.Y.) was used as the plastic mold. The water is then removed by freeze-drying using a Labconco freeze-dryer (model 77580, Kansas City, Mo.). By this technique, a fibronectin-HPC wound dressing with a sponge-like structure is produced.

Example 4

Solid Carbomer Dressing

A solid carbomer dressing was prepared using Carbopol® 974P NF carbomer (BF Goodrich, Cleveland, Ohio) as the preferred grade. A solid wound dressing containing (w/w) fibronectin 75%, carbomer 25% was prepared as follows. 2.80 g of carbomer was dispersed in 97.2 mL of demineralized water and mixed with a paddle type stirrer for about 3 hours. This dispersion is then autoclaved to provide a sterile concentrated hydrogel base (2.80% w/w). 50 mg of lyophilized human plasma fibronectin, prepared according to Example 10, were dissolved in 5 mL of deionized water containing 12 μL of NaOH 3M, pH 11.6. The solution was maintained at 37° C. until complete solubilization of fibronectin occurred. This stock solution of fibronectin (10 mg/mL) was filtered through a 0.22 μm acetate filter. 3.3 mL of the fibronectin solution was then added to 0.04 g of concentrated carbomer base and the necessary amount of gelifying promoter (25 μL NaOH 3M) and mixed with syringes as described in Example 1. This fibronectin carbomer hydrogel is deposited in a plastic mold and frozen. A Costar 6-well polystyrene cell culture cluster, 9.6 $cm^2$ rounded surface area (Corning Inc., Corning, N.Y.) was used as the plastic mold. The water is then removed by freeze-drying using a Labconco freeze-dryer (model 77580, Kansas City, Mo.). By this technique, a fibronectin-carbomer wound dressing with a sponge-like structure is produced.

Example 5

Solid Carrageenan Dressing

Solid carrageenan dressing was prepared. The preferred grade is Gelcarin® NF carrageenan (FMC Corporation Pharmaceutical Division, Newark, Del.). A solid wound dressing containing (w/w) fibronectin 73%, carbomer 27% was prepared as follows. 2.50 g of carrageenan was dispersed in 97.5 mL of deionized water and allowed to be mixed with a paddle type stirrer for about 3 hours. This dispersion is then autoclaved to provide a sterile concentrated hydrogel base (2.50% w/w). 50 mg of lyophilized human plasma fibronectin, prepared according to Example 10, were dissolved in 5 mL of deionized water containing 12 µL of NaOH 3M, pH 11.6. The solution was maintained at 37° C. until complete solubilization of fibronectin occurred. This stock solution of fibronectin (10 mg/mL) was filtered through a 0.22 µm acetate filter. 3.3 mL of fibronectin solution was then added to 0.50 g of concentrated carrageenan base and mixed with syringes as described in Example 1. The pH is adjusted to 7.0 with the addition of 60 µL HCl 1 N. At this point, the homogenous solution of the fibronectin-carrageenan complex is deposited in a plastic mold and frozen. A Costar 6-well polystyrene cell culture cluster, 9.6 cm$^2$ rounded surface area (Corning Inc., Corning, N.Y.) was used as the plastic mold. The water is then removed by freeze-drying using a Labconco freeze-dryer (model 77580, Kansas City, Mo.). By this technique, a fibronectin-carrageenan wound dressing with a sponge-like structure is produced.

Example 6

In Vitro Study of Solid Wound Dressings

In vitro study of the absorption of fibronectin in deepithelialized human skin using a cell diffusion system showed that up to 91.7% of the fibronectin is released within a 12-hour period (see FIG. 1) from a fibronectin-calcium alginate dressing prepared as follows: 10.0 gram of sodium alginate (Protanal LF 10/60, Pronova Biopolymer, Drammen, Norway) is dispersed in 90 g of deionized and demineralized water with a paddle type stirrer for about one hour. This dispersion is then autoclaved to provide a sterile concentrated alginate base (10% w/w). 10 mL of a 1.0% fibronectin stock solution is filtered through a 0.22 µm acetate filter and mixed into syringes with 5 mL of a 1% sodium alginate solution in mild acetic acid, prepared from a concentrated alginate base. The gellation of the solution is achieved by adding 375 µL of (0.2M NaCl+0.2 M CaCl$_2$) plus 30 µL of 17.45 N acetic acid for a final pH of 4.0. At this point, the homogenous solution of the fibronectin-calcium alginate complex is deposited in a plastic mold and frozen. A Costar 6-well polystyrene cell culture cluster, 9.6 cm$^2$ rounded surface area (Corning Inc., Corning, N.Y.) was used as the plastic mold. The water is then removed by freeze-drying using a Labconco freeze-dryer (model 77580, Kansas City, Mo.). By this technique, a fibronectin-calcium alginate wound dressing with a sponge-like structure is produced. After freeze-drying, the surface area of the final disk is close to 8.96 cm$^2$ surface area because the disk shrinks during freeze-drying. The amount of fibronectin in the 5 mL formulation is 33.3 mg for a concentration of 37 µg/mm$^2$ of surface area (33,333 µg/896 mm$^2$).

This fibronectin-calcium alginate dressing was compared to the solid wound dressings dressing of Examples 2–5 for 12 hours in deepithelialized skin diffusion cell system. The deepithelialized skin diffusion cell system utilized in the experiments shown in FIG. 1 is described in Beaulieu, U.S. Pat. No. 5,877,149, issued Mar. 2, 1999, which is incorporated herein by reference.

The amount released represents 34.1 µg of fibronectin per mm$^2$ deepithelialized skin surface area and is a significant increase (262%) compared with the 13.0 µg fibronectin released from 1.0% fibronectin carbomer hydrogel after 12 hours, as described in U.S. Pat. No. 5,821,220 incorporated herein by reference. The amount of fibronectin released from the fibronectin-cellulose derivatives of Example 2 and 3 were similar with those obtained with fibronectin-calcium alginate (see FIG. 1). However, once hydrated with saline solution, the fibronectin-cellulose dressings do not provide the desired fibrous protective film on the surface of the deepithelialized human skin.

Example 7

The Rabbit Ear Dermal Ulcer Model

A study of the efficacy of the fibronectin-calcium alginate wound dressing in stimulating wound healing was performed using the rabbit ear dermal ulcer model of wound healing as developed by Mustoe et al. (1991) J. Clin Invest 87: 694–703.

Young adult New Zealand white rabbits, 3.0–3.5 kg (Charles River Laboratories, Canada) were anesthetized with ketamine (60 mg/kg) and xylazine (95 mg/kg). Using a 6-mm trephine and microsurgical instruments, four circular full-thickness 6-mm diameter ulcers were made to the depth of bare cartilage under sterile conditions. As cartilage is non-vascularized, new granulation tissue formation occurs only at the periphery of the ulcer.

6 mm-diameter pieces of solid dressings were applied immediately after surgery. Alginate dressing (Kaltostat, ConvaTec, Skillman, N.J.), collagen-alginate dressing (Fibracol, Johnson & Johnson, Arlington, Tex.) and fibronectin-calcium alginate dressing were applied on the ulcers and wetted with 40 µL of saline solution (Aqualite® 0.9% sodium chloride solution). The fibronectin-calcium alginate dressing was prepared according to the method described in Example 1. Control treatment (identified in FIGS. 2–5) were ulcers treated with 40 µL of saline alone. The wounds were covered with an occlusive polyurethane film (Tegaderm film, 3M, Minneapolis, Minn.) to prevent wound desiccation. Neck collars were placed on rabbits for the duration of the experiment. Differences in rates of healing between treatment groups were measured at day 7.

A. Histomorphometric Measurement of New Granulation Tissue

At the time of killing, the ulcers were bisected and fixed in 10% buffered formalin. The specimens were then dehydrated in graded alcohol and xylene, embedded in paraffin, and sectioned, taking care to obtain a cross section as near as possible to the center of the wound. After Masson-trichrome staining of 3-µm sections, the granulation tissue gap (GAP) (defined as the remaining diameter of the wound without new granulation tissue) and the maximum height (MH) of the new granulation tissue at the advancing edges of the wound were measured by histomorphometry using Biometrics Bioquant true color laser vision (R&M, Nashville, Tenn.). Each MH value represents the mean of four measurements of the maximum height of the new granulation tissue for the right and the left side of two tissue sections for each ulcer.

The GAP distance is used to calculate the surface area of the wound by the equation $(GAP/2)^2\pi$. On day 0 (day of surgery), the measured GAP was 6.2 mm and the area was $(6.2/2)^2\pi=30.19$ mm². New granulation tissue surface area is the area of wound at day 0 minus the area of wound at day 7, i.e., (GAP [day 0]/2)²π–(GAP [day 7]/2)²π The new granulation volume (NGV) is new tissue surface area×MH. Area and volume measurements for new granulation tissue were calculated based on the assumptions that the wounds healed concentrically and did not contract. Statistical analysis was carried out using a Student's paired t test for each formulations studied using Excel version 5.0 (Microsoft Corporation). All comparisons were made to paired control wounds (saline, alginate or collagen-alginate). P<0.05 was considered significant.

Figure 2:
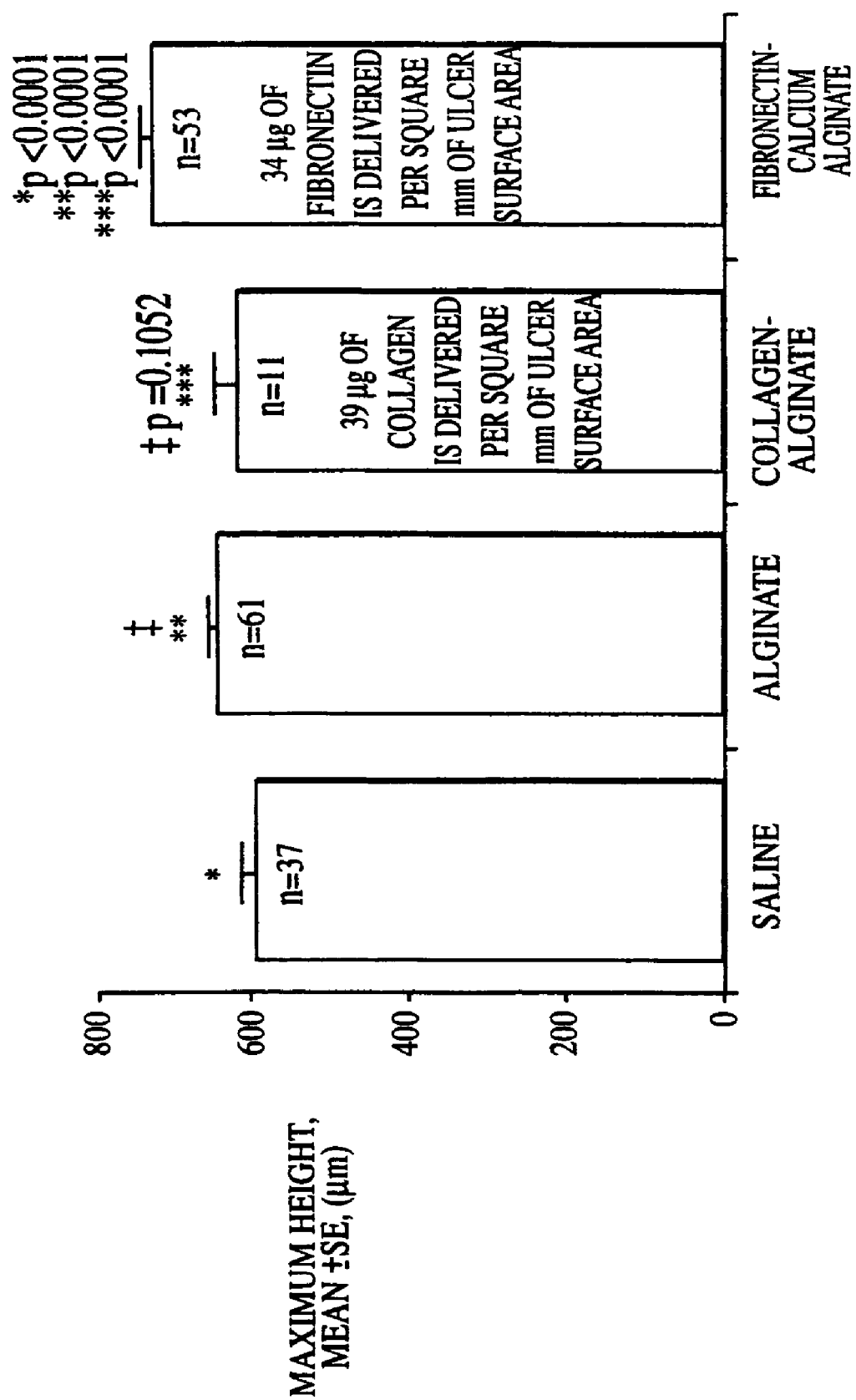
FIG. 2 depicts new granulation tissue formation, measured as maximum height (μm) in response to treatment with a fibronectin-calcium alginate dressing after 7 days of treatment. 6-mm diameter dressings were applied at the time of surgery. Alginate dressing (Kaltostat), collagen-alginate dressing (Fibracol) and fibronectin-calcium alginate dressings were placed on the ulcers and wetted with 40 μL of saline solution. Control treatment (identified as †"saline") were ulcers treated with 40 μL of saline alone. Occlusive dressings (Tegaderm) were used to prevent wound desiccation. The fibronectin-calcium alginate dressing (n=53) was significantly better than saline (P<0.0001, n=37), alginate (P<0.0001, n=61) or collagen-alginate (P<0.0001, n=11). No difference was observed between alginate and collagen-alginate dressing (P=0.1052) using Student two-tailed t test. Bars represent standard errors of the mean.
Figure 3:
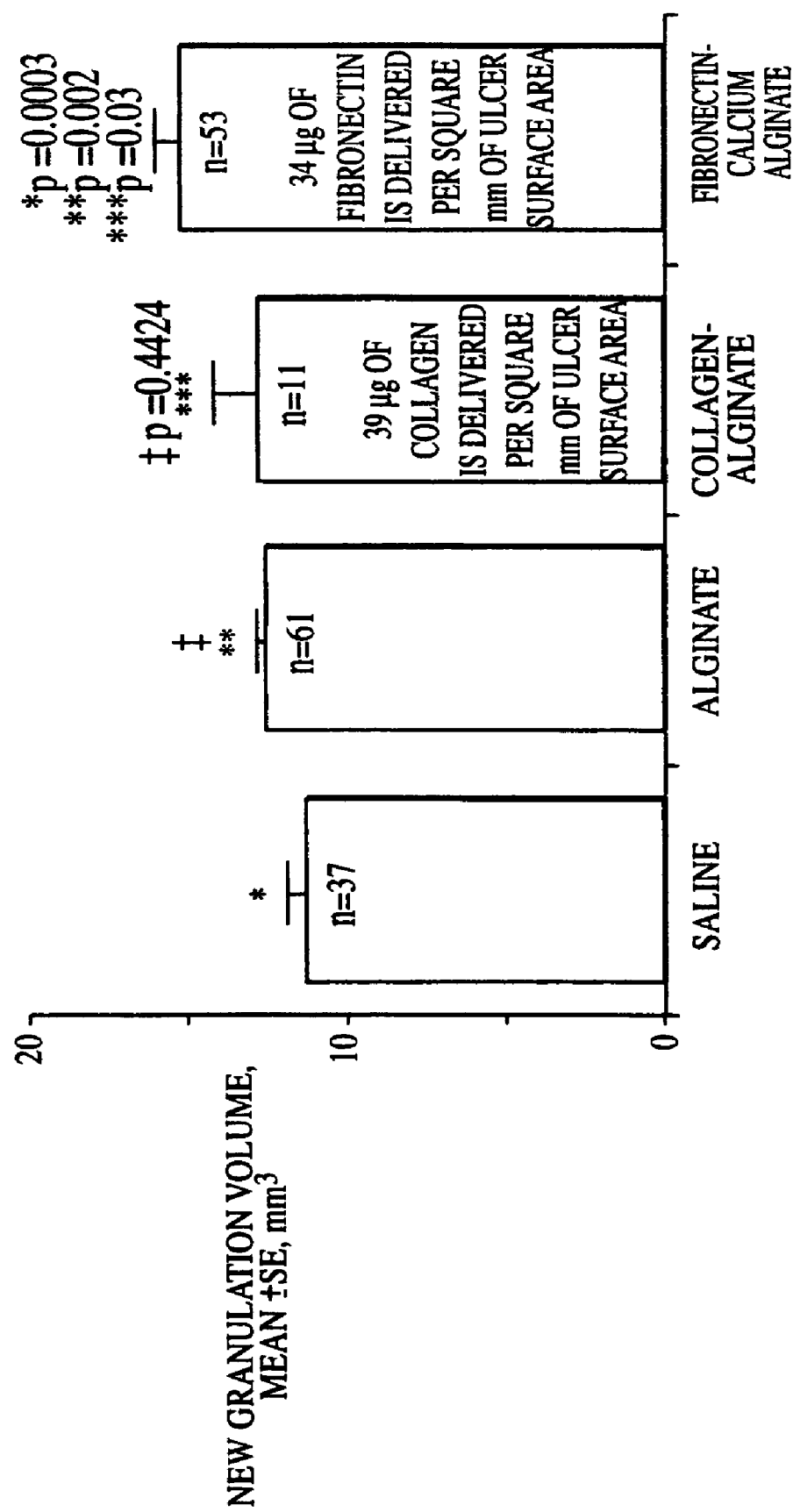
FIG. 3 illustrates the new granulation volume formed in response to treatment with fibronectin-calcium alginate dressing after 7 days of treatment. 6-mm diameter dressings were applied at the time of surgery. Alginate (Kaltostat), collagen-alginate (Fibracol) and fibronectin-calcium alginate dressings were placed on the ulcers and wetted with 40 μL of saline solution. Control treatment (identified as †"saline") were ulcers treated with 40 μL of saline alone. Occlusive dressings (Tegaderm) were used to prevent wound desiccation. The fibronectin-calcium alginate dressing (n=53) was significantly better compared to saline (P<0.0003, n=37), alginate (P<0.002, n=61) or collagen-alginate (P<0.03, n=11) dressing in stimulating new granulation tissue formation. No difference was observed between alginate and collagen-alginate dressing (P=0.4424) using Student two-tailed t test. Bars represent standard errors of the mean.

B. Effect of Fibronectin Calcium Alginate Dressing Containing 65% Fibronectin (w/w) in Stimulating New Granulation Tissue Formation Results of histomorphometric measurements show that the effect of a single application of the fibronectin-calcium alginate dressing, produced according to the method of Example 6, was significantly better than alginate (Kaltostat) or collagen-alginate (Fibracol) dressings in generating new granulation tissue in the rabbit ear dermal ulcer model. This amount of fibronectin delivered represents approximately 34 μg per mm² rabbit surface ulcer area whereas a dose of 39 μg per mm² of collagen was used for collagen-alginate dressing. As shown in FIG. 2, after 7 days of treatment, the maximum height (MH) for fibronectin-calcium alginate treated wounds was significantly higher compared to the control wounds (732±13 μm vs 599±16 for saline, 648±11 for alginate and 621±27 for collagen-alginate treated wounds, P<0.0001 in all cases). For the new granulation volume (NGV) values, significant increases (more than 120% compared to collagen-alginate, 122% compared to alginate and 137% compared to saline) were observed for the fibronectin-calcium alginate (FIG. 3). The calculated values were respectively 15.02±0.77 mm³ for fibronectin-calcium alginate, 10.95±0.76 for saline, 12.29±0.59 for alginate and 12.46±1.47 collagen-alginate. Neither alginate nor collagen-alginate dressings were significantly different for the MH values (P=0.1052) and NGV values (P=0.4424) when compared to each other or saline.

C. Effect of 1.0% Fibronectin-Carbomer Hydrogel

Treatment with fibronectin in a 1.0% fibronectin-carbomer hydrogel formulation on the rabbit dermal ulcer model was evaluated in its capacity to stimulate the formation of new granulation tissue. The fibronectin was applied as a 0.281% carbomer hydrogel, applying a volume of 40 μL of hydrogel containing 400 μg of fibronectin. The 1.0% fibronectin-carbomer hydrogel prepared according to Example 9, pH 11.6. This delivered approximately 13 μg of fibronectin per mm² rabbit ulcer surface area as described in U.S. Pat. No. 5,821,220. The fibronectin-carbomer hydrogel was applied to the test ulcer once a day for a period of 7 days, starting at the time of surgery. The volume of topical formulations applied to the control wounds (saline or 0.281% carbomer hydrogel containing no fibronectin) was also 40 μL. Antiseptic tulle gras dressing (Bactigras®, Smith & Nephew, Lachine, Canada) and a non-adherent absorbent dressing (Melolite®, Smith & Nephew, Lachine, Canada) were used to prevent wound desiccation. Before each daily application, the ulcers were washed with sterile saline solution, gently cleaned with a moistened cotton-swab.

Figure 4:
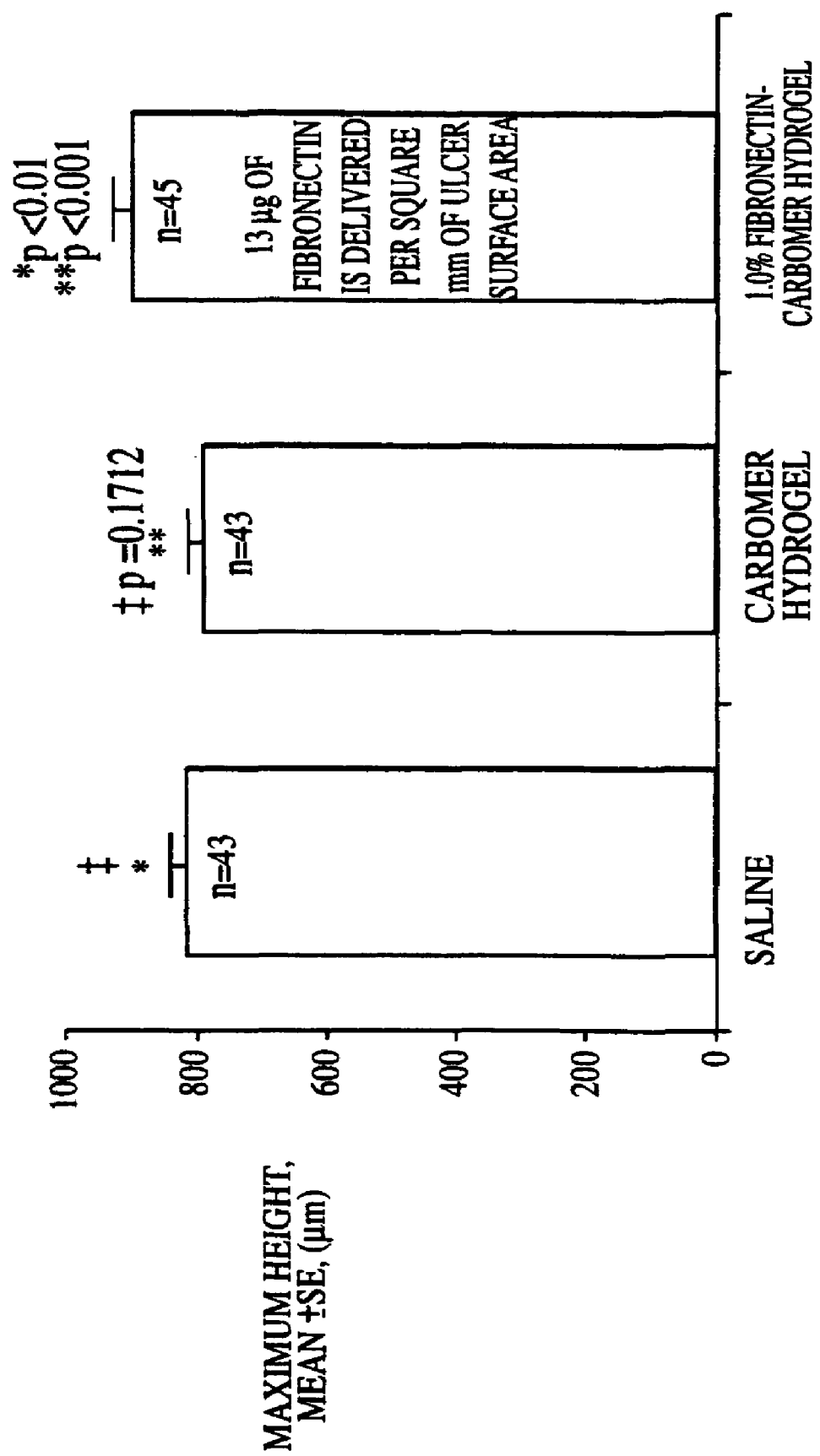
FIG. 4 shows new granulation tissue formation, measured as maximum height (μm) in response to 1.0% fibronectin carbomer hydrogel after 7 days of treatment. The fibronectin was applied as a 0.281% carbomer hydrogel (40 μL containing 400 μg of fibronectin) at the time of the surgery and daily during 7 days. The volume of the topical formulations applied to control wounds (saline and 0.281% carbomer hydrogel) was also 40 μL. Antiseptic tulle gras dressing (Bactigras) and non-adherent absorbent dressing (Melolite) were used to prevent wound desiccation. The 1.0% fibronectin-carbomer hydrogel treatment (n=45) was significantly better than either saline (P=0.01, n=43) or carbomer hydrogel containing no fibronectin in stimulating new granulation tissue formation (P=0.001, n=43). No difference was observed between saline and carbomer hydrogel alone (P=0.1752) using Student two-tailed t test. Bars represent standard errors of the mean.
Figure 5:
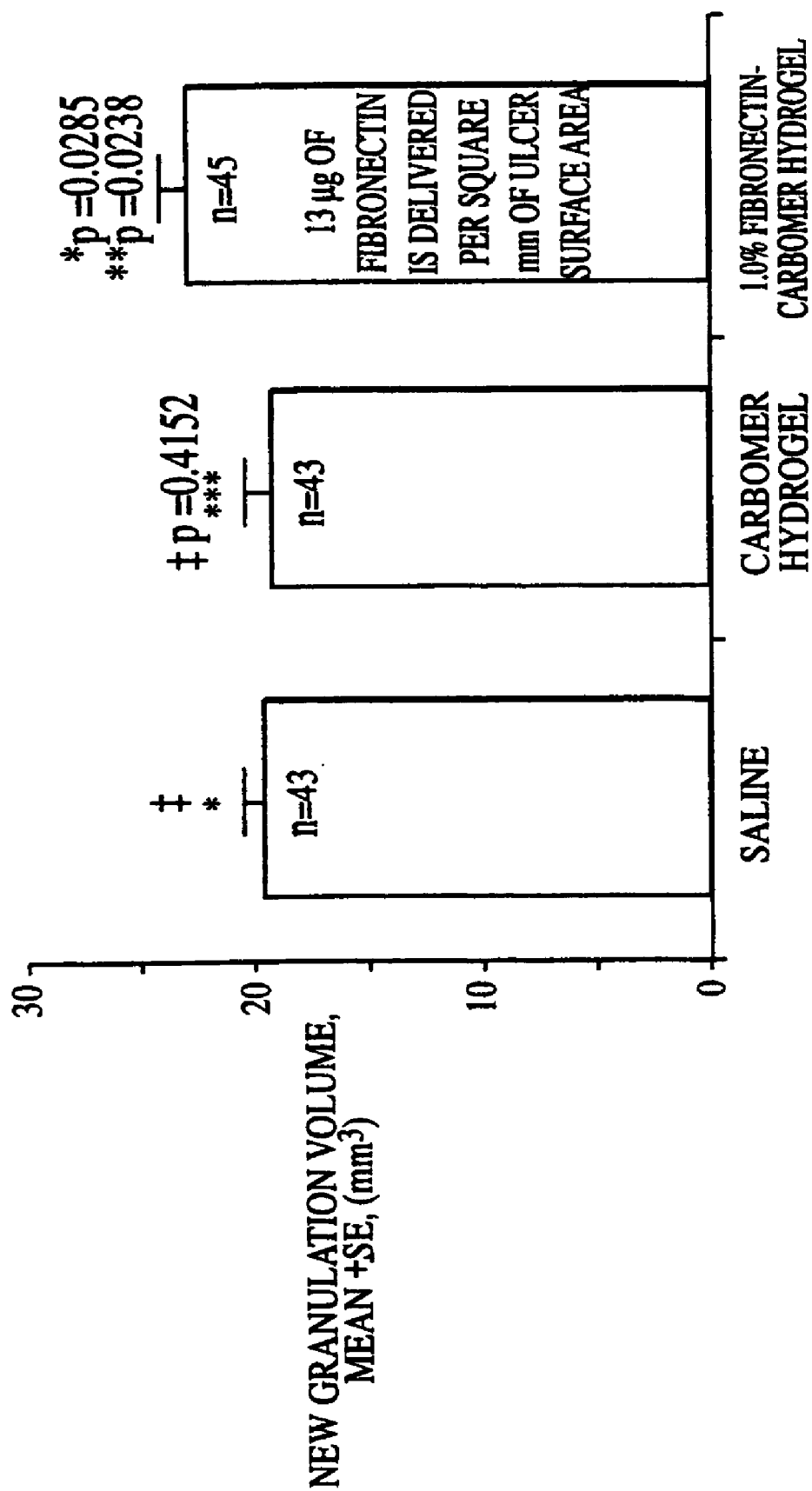
FIG. 5 illustrates the new granulation volume in response to 1.0% fibronectin carbomer hydrogel after 7 days of treatment. The fibronectin was applied as a 0.281% carbomer hydrogel (40 µL containing 400 µg of fibronectin) at the time of the surgery and daily during 7 days. The volume of the topical formulation applied to the control wounds (saline and 0.281% carbomer hydrogel) was also 40 µL. Antiseptic tulle gras dressing (Bactigras) and non-adherent absorbent dressing (Melolite) were used to prevent wound desiccation. The 1.0% fibronectin-carbomer hydrogel treatment (n=45) was significantly better when compared to saline (P=0.0285, n=43) and carbomer hydrogel containing no fibronectin (P=0.0238, n=43) in stimulating new granulation tissue formation. No difference was observed between saline and carbomer hydrogel alone (P=0.4152) using Student two-tailed t test. Bars represent standard errors of the mean.

When the histomorphometric measurements were analyzed, they revealed that the mean maximum height of new granulation tissue in fibronectin-carbomer hydrogel-treated wounds (900±30 μm, n=45) was significantly higher when compared to treatment with either saline (819±23 μm, n=43, P=0.01) or carbomer hydrogel containing no fibronectin (793±19 μm, n=43, P=0.001), (FIG. 4). Furthermore, the volume of new granulation tissue formation was significantly greater with 1.0% fibronectin-carbomer hydrogel treatment (21.22±1.14 mm³, n=45) when compared to saline (18.67±0.79 mm³, n=43, P=0.0285) or carbomer hydrogel containing no fibronectin (18.43±0.95 mm³, n=43, P=0.0238, (FIG. 5). No difference was observed between saline and carbomer hydrogel alone. (P=0.4152)

D. Dosage Testing of Fibronectin

A study of the effects of varying doses of fibronectin on wound healing was conducted in a rabbit model using techniques as described above. However, in these experiments, a 9-mm AcuPunch® biopsy punch was used to produce the model ulcers in the rabbit ear. Four wounds were made in each ear of each experimental animal. One ear was treated with the saline control dressing and the other ear was treated with the fibronectin calcium-alginate dressing as described above. The fibronectin-calcium alginate disks for this experiment are prepared as in Example 1. The disks were stacked and if necessary cut to provide the following dosages of fibronectin, 10.3 μg/mm², 20.6 μg/mm², 41.25 μg/mm², 82.5 μg/mm², 123.75 μg/mm², 165 μg/mm². The results of varying dosages on maximum height (MH) and new granulation volume (NGV) are shown respectively, in Tables 1 and 2 below. Clear benefit from the presence of fibronectin-calcium alginate disks was demonstrated and the effect appears to be dose related, particularly in the range of 10 to 120 μg/mm².

TABLE 1

Summary of the Fibronectin effect on MH

|  | Nb Rabbits | Nb ulcers Per group | Control group mean MH (mm) | Treatment group mean MH (mm) | p-value |
| --- | --- | --- | --- | --- | --- |
| 10.3 μg/mm² | 12 | 48 | 0.75 | 0.78 | p = 0.248 |
| 20.6 μg/mm² | 13 | 52 | 0.76 | 0.85 | p < 0.0001 |
| 41.25 μg/mm² | 12 | 48 | 0.69 | 0.77 | p < 0.0001 |
| 82.5 μg/mm² | 13 | 52 | 0.67 | 0.79 | p < 0.0001 |
| 123.75 μg/mm² | 12 | 48 | 0.69 | 0.82 | p < 0.0001 |
| 165 μg/mm² | 12 | 48 | 0.66 | 0.80 | p < 0.0001 |

TABLE 2

Summary of the Fibronectin effect on NGV

|  | Nb Rabbits | Nb ulcers Per group | Control group mean NGV (mm³) | Treatment group mean NGV (mm³) | p-value |
| --- | --- | --- | --- | --- | --- |
| 10.3 μg/mm² | 12 | 48 | 16.34 | 15.91 | p = 0.612 |
| 20.6 μg/mm² | 13 | 52 | 19.66 | 20.53 | p < 0.282 |
| 41.25 μg/mm² | 12 | 48 | 15.52 | 17.90 | p < 0.0008 |
| 82.5 μg/mm² | 13 | 52 | 15.13 | 18.26 | p < 0.0001 |
| 123.75 μg/mm² | 12 | 48 | 16.19 | 19.75 | p < 0.0001 |
| 165 μg/mm² | 12 | 48 | 14.36 | 15.80 | p < 0.104 |

Figure 6:
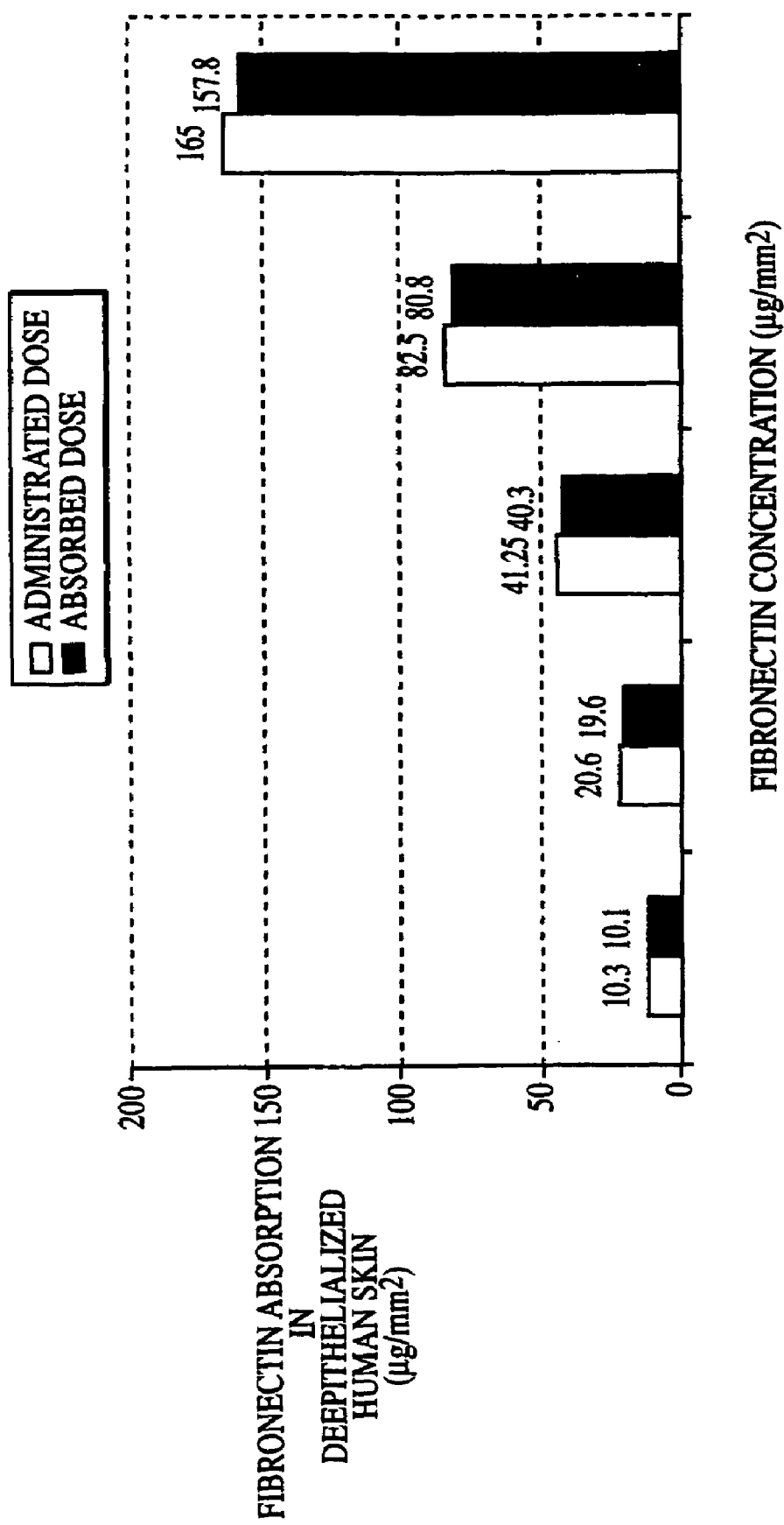
FIG. 6 illustrates the amount of fibronectin absorbed from fibronectin-calcium alginate disks prepared according to Example 1 for various tested amounts of fibronectin. Absorption was measured using the human deepithelialized skin diffusion cell system after 24 hours.

An in vitro study, in the deepithelialized skin diffusion cell system, of fibronectin absorption for varying applied doses from 10.3 to 165 μg/mm² using the fibronectin-sodium alginate disks of Example 1 was also conducted. The results are shown in FIG. 6.

Example 8

Calcium-Alginat Disks for Delivery of High Concentrations of Human Plasma Fibronectin A preferred delivery system of the invention consists of human plasma fibronectin lyophilized in the presence of calcium-alginate to form solid disks, which are to be applied topically to the wound surface to be treated. As opposed to liquid formulations containing fibronectin, the use of calcium-alginate disks helps insure the delivery of known, consistent amounts of fibronectin to a wound surface.

In one embodiment of the invention, human fibronectin is purchased as a cryoprecipitate from a licensed manufacturer (MedImmune, Maryland through DCI Management, New York, N.Y.). The cryoprecipitate extract is first dissolved and clarified. The cryoprecipitate extract is then treated to inactivate lipid enveloped viruses by the solvent/detergent procedure using 0.3% tri (n-butyl) phosphate (TNBP) and 1% Triton X-100 for four hours at room temperature. The process reagents are removed and the fibronectin is purified on a gelatin-Sepharose affinity chromatography. Bound fibronectin is eluted from the column with 1M potassium bromide at pH 5.0. Following the removal of salts, the fibronectin is concentrated by 100 KD membrane ultrafiltration. sterilized using a 0.22 µm acetate filter and lyophilized. It is then combined with sterile calcium-alginate as described in Example 1. Sterile glass vials are filled aseptically with 5 mL of the fibronectin/calcium alginate mixture under Food and Drug Administration, class 100 good manufacturing procedures.

Stoppers should be inserted partway into the vials and the preparation is dried on a FTS Duralyophilizer lyophilizer. In a preferred embodiment of the invention, the prepared disks, 4.2 cm$^2$ in diameter, are removed from the vial by forceps, placed on the wound to be treated and wetted with sterile saline (0.9% NaCl). Each dressing holds 80 µg of fibronectin per mm$^2$ of surface area. More than one dressing may be used depending on the size of the skin ulcer or other lesion to be treated and must be trimmed to fit the shape of the wound. The disks may be stacked to deliver larger doses of fibronectin, such as 160 µg per mm$^2$, 240 µg per mm$^2$, and so forth.

The dressings according to this and previous examples can be prepared using fibronectin from a non-human source. Representative animals include, but are not limited, to horses, dogs and cats.

In one preferred method of treating a human or animal patient, no other ointments, creams or dressings are applied to the wound, ulcer or other lesion while the fibronectin-solid wound dressing of this example is used. The dressing is preferably applied with high compression therapy using a long stretch four-layer bandage.

For example, in a leg lesion, the foot of the patient's bed that is used for sleeping should be raised to form an angle of about 20 degrees. For example, a two-inch block can be placed under the foot of a human patient's bed or two pillows can be placed between the base and the mattress of the bed. If the patient remains seated or lying down for more than 30 minutes after application, he/she should raise his/her legs. Similarly, if the patient remains in a fixed standing position after application, he/she must walk every 30 minutes.

Twice a week, the dressing according to the invention is removed and the wound bed is inspected for evidence of infection. If there are signs of infection, they should be evaluated and treated as necessary by the appropriate health care practitioner. If there is no evidence of infection, then the wound bed is assessed as follows. If at least 50% of the wound bed is pale pink to beefy red (as opposed to gray, yellow, or black indicating necrotic material), then the replacement dressing and compression are applied. If less than 50% of the ulcer bed is pink or red, the wound bed should be debrided, i.e. cleaned of any necrotic material. Debridement should be done with sharp surgical instruments and can be done using local anesthesia.

Example 9

Solubility of Fibronectin

To prepare 10 g of fibronectin carbomer hydrogel, the following ingredients must be added in sequence. First, the pH of 8.8 mL demineralized water, pH 5.0, is adjusted to pH 8.0 to 11.0 by adding 2.95 µg to 2.95 mg NaOH 3M. Demineralized water from different sources may have different starting pH values and the exact amount of NaOH 3M can be adjusted as need to the desired value.

Next, 0.05 to 0.1 grams of lyophilized fibronectin are dissolved in the demineralized water, pH 8.0 to 11.0. In a final step of the procedure, 1 mL of water containing 0.028 g of carbomer and 0.09399705 g to 0.09105 g of NaOH 3M are added to the mixture. Examples of the composition for several fibronectin carbomer hydrogels are shown in Table 2. "FN" stands for lyophilized fibronectin.

TABLE 3

| Composition of fibronectin carbomer hydrogels Stock solution of carbomer | | | |
|---|---|---|---|
| 3.75% | | 2.80% | |
| 10 g (0.5% FN/0.28% Carbomer) | 10 g (1.0% FN/0.28% Carbomer) | 10 g (0.5% FN/0.28% Carbomer) | 10 g (1.0% FN/0.28% Carbomer) |
| 0.75 g Carbomer | 0.75 g Carbomer | 1.00 g Carbomer | 1.00 g Carbomer |
| 0.05 g FN | 0.1 g FN | 0.05 g FN | 0.1 g FN |
| 9.106 g water | 9.056 g water | 8.856 g water | 8.806 g water |
| 0.094 g NaOH 3 M | 0.094 g NaOH 3 M | 0.094 g NaOH 3 M | 0.094 g NaOH 3 M |

| Stock solution of carbomer | | | |
|---|---|---|---|
| 3.75% | | 2.80% | |
| 20 g (0.5% FN/0.28% Carbomer) | 20 g (1.0% FN/0.28% Carbomer) | 20 g (0.5% FN/0.28% Carbomer) | 20 g (1.0% FN/0.28% Carbomer) |
| 1.50 g Carbomer 0.1 g FN 18.212 g water 0.188 g NaOH 3 M | 1.50 g Carbomer 0.2 g FN 18.112 g water 0.188 g NaOH 3 M | 2.00 g Carbomer 0.1 g FN 17.712 g water 0.188 g NaOH 3 M | 2.00 g Carbomer 0.2 g FN 17.612 g water 0.188 g NaOH 3 M |

In a particularly preferred embodiment of the fibronectin gel of the invention, the following ingredients must be added in this sequence. First, the pH of demineralized water (8.856 or 8.806 grams) is adjusted to 11.6 with 0.0235 grams of NaOH 3M. 8.856 grams of water is utilized when 0.05 grams of fibronectin will be added; 8.806 grams of water is utilized when 0.1 grams of fibronectin will be added. 0.05 or 0.1 grams of lyophilized fibronectin is next dissolved in the demineralized basic water. In a final step of the procedure, 0.028 grams of carbomer and 0.0705 grams of NaOH 3M are added to the mixture. The 0.028 grams of carbomer comes from 1.0 gram of a 2.8% carbomer stock solution. The concentrated carbomer stock solution may be at 3.75% or 2.80%. The preparation of fibronectin carbomer hydrogels using different concentrated stock solutions is illustrated in Table 2. A preferred grade of carbomer is Carbopol® 974P NF carbomer (BF Goodrich, Cleveland, Ohio). The fibronectin concentration is measured by the well-known micro-Bradford method. The Bradford protein assay is based upon the Bradford dye-binding procedure (Bradford, M. Anal. Biochem. 72, 248, 1976). The protein assay is based on the color change of Coomassie® Brillant Blue G-250 dye, in response to various concentrations of protein.

TABLE 5

Solubility of fibronectin in water containing varying concentrations of NaOH ($10^{-7}$ M to $10^{-3}$ M) with corresponding pH (7.0 to 11.0)

| Lyophilized fibronectin (mg) | Measured concentration of fibronectin (micro-Bradford method) (1 h/37° C. in water + NaOH) (mg/mL) | | | | |
|---|---|---|---|---|---|
| | $10^{-7}$ M NaOH; pH 7.0 | $10^{-6}$ M NaOH; pH 8.0 | $10^{-5}$ M NaOH; pH 9.0 | $10^{-4}$ M NaOH; pH 10.0 | $10^{-3}$ M NaOH; pH 11.0 |
| 10 | 8.0 (1)* | 8.5 (1) | 9.2 ± 0.5 (2) | 8.7 (1) | 9.2 ± 0.3 (5) |

*The number in parentheses refers to the number of experiments performed

Example 10

Solvent/Detergent-Treated human Homologous Plasma Fibronectin

The lyophilized fibronectin used in Examples 1–7 and 9 was prepared as described in this example.

First, lots of plasma prepared from different donors are tested for atypical antibodies, hepatitis B and C virus (HBV,

TABLE 4

Solubility of fibronectin in non-buffered water (pH 5.0–6.0) compared to the solubility of fibronectin in water with NaOH 0.007 M, pH 11.6

| Lyophilized fibronectin (mg) | Measured concentration of fibronectin (micro-Bradford method) (1 h /37° C. in water) (mg/mL) | Measured concentration of fibronectin (micro-Bradford method) (12 h /37° C. in water) (mg/mL) | Measured concentration of fibronectin by (micro-Bradford method) (24 h /37° C. in water) (mg/mL) | Measured concentration of fibronectin by (micro-Bradford method) (1 h /37° C. in water + NaOH) (mg/mL) |
|---|---|---|---|---|
| 4 | 2.1 ± 0.4 (3)* | 2.7 ± 0.4 (3) | 3.0 ± 0.3 (4) | 4.1 ± 0.2 (3) |
| 10 | 5.7 ± 0.4 (3) | 6.3 ± 0.2 (3) | 5.7 ± 0.3 (4) | 9.0 ± 0.3 (4) |
| 15 | 7.1 (1) | 7.5 (1) | — | — |
| 20 | 7.3 (1) | 8.5 (1) | — | 14.1 (1) |

*The number in parentheses refers to the number of experiments performed

HCV), human immunodeficiency virus (HIV), human T-cell lymphotrophic virus (HTLV), cytomegalovirus (CMV) and syphilis.

Second, a viral inactivation solvent/detergent method using tri(n-butyl)phosphate (TNBP) and Triton X-100 is performed. Treatment of plasma products with organic solvent, tri(n-butyl)phosphate (TNBP) and Triton X-100 detergent was shown to inactivate very large quantities of HBV, HCV and HIV (Horowitz et al., 1992, Blood 79 (3):826–31 without affecting labile proteins such as fibronectin.

In a typical preparation, frozen plasma from 5 donors is thawed and treated while stirring for 6 hours with 1% (vol/vol) TNBP, 1% (vol/vol) Triton X-100 and 1 mM phenylmethylsulfonyl fluoride at 24° C. After treatment, soybean oil (20% vol/vol) is added, mixed gently for 30 minutes at ambient temperature, and then removed by using a decantation funnel at 4° C.

Once fibronectin is purified from plasma, for example by the gelatin-Sepharose affinity chromatography procedure described below, the final solution is verified for contamination by TNBP and Triton X-100. TNBP is quantified in a sample of purified fibronectin after hexane extraction by gas chromatography using a 0.25-in by 2 mm ID by 4-ft glass column packed with 10% SP-1000 on a 80/100 mesh Supelcoport (Supelco, Bellafonte, Pa.). Triton X-100 was assayed by injecting a sample of purified fibronectin to high liquid chromatography (HPLC) on a gel filtration column G2000 SW 7.5 mm ID by 60 cm (Tosohass) coupled with a UV detector set at 230 nm. Fibronectin preparations were found to contain less that 1 ppm of either TNBP or Triton X-100.

Fibronectin was isolated from solvent/detergent-treated human plasma using a gelatin-Sepharose affinity chromatography procedure (Horowitz and Chang, 1989). This method takes advantage of the affinity of fibronectin for gelatin in a procedure that allows isolation of electrophoretically pure fibronectin from human plasma with excellent yields.

In this method, gelatin is covalently coupled to Sepharose CL-4B after CNBr activation. The binding capacity for human plasma fibronectin provided by this system is >1 mg/mL of gel. The purificaton is performed in a batch procedure with a glass funnel filter holder (Costar Nucleopore, Pleasanton, Calif.) with a capacity of 375 mL and a filtration area of 10.5 cm$^2$ at a flow rate of 25 mL/min.

Briefly, the plasma sample is passed twice on a gelatin-Sepharose gel. The matrix is washed with several volumes of 0.15 M Tris-HCl buffer pH 7.5, several volumes of 0.15 M Tris-HCl buffer pH 7.5+1 M NaCl and again with 0.15 M Tri-/HCl buffer pH 7.5. Elution is carried out with 1 M KBr in 0.1 M acetate buffer pH 5.0. The resulting solution of fibronectin is then exhaustively dialyzed against deionized and demineralized water, ultrafiltered under nitrogen, lyophilized and frozen at −80° C. until used.

The protein concentration is determined using the Bio-Rad protein assay (Bio-Rad Laboratories, Richmond, Calif.). The following diagram summarizes the purification steps.

Fibronectin from non-human animals can be purified using similar methods. The lots of plasma would be screened for atypical antibodies as appropriate for the source organism and known to those skilled in the art.

For example, domestic cat plasma would be screened for feline leukemia virus.

| Procedures for purifying fibronectin from human plasma treated with TNBP/Triton X-100 |
|---|
| 2.5 L of plasma (from 5 donors) |
| 1.0% (v/v) TNBP + |
| 1.0% (v/v) Triton X-100 |
| 6 hr/24° C. |
| Solvent-Detergent plasma |
| TNBP extraction with 20% (v/v) |
| vegetable oil |
| Plasma + 200 mL of gelatin-Sepharose gel |
| First wash Tris-HCl buffer 0.15 M pH 7.5 |
| Second wash Tris-HCl buffer 0.15 M + 1 M NaCl pH 7.5 |
| Third wash Tris-HCl buffer 0.15 M pH 7.5 |
| Elution sodium acetate buffer 0.1 M + 1 M KBr pH 5.0 |
| Dialysis against deionized and demineralized water |
| Concentration by ultrafiltration under nitrogen |
| Sterile filtration with 0.22 μm acetate filter |
| Lyophilization |

Example 11

Dry heat Treatment of Plasma Fibronectin (Pasteurization)

The viral inactivation solvent/detergent method (25° C. for 6 h) as described in the previous example has been recognized to be highly effective in the destruction of enveloped-viruses. According to Radosevich (Seminars in Thrombosis and Hemostasis. 24 (2) 157–161,1998), pasteurization has broader virucidal action owing to its additional ability to inactivate non-enveloped viruses. Non-enveloped viruses are usually more resistant to physicochemical treatments than enveloped viruses. Thus, improvements in viral safety for plasma products may be obtained by combining different viral reduction procedures (e.g. solvent-detergent+dry heat treatments).

An additional dry heat treatment on lyophilized solvent-detergent treated-fibronectin at 68° C. for 96 hours can be performed before incorporating the fibronectin in the wound formulations of the invention described in the previous examples. For example, in one embodiment of the invention, 50 mg of lyophilized fibronectin prepared according to Example 10 was placed in a 50 mL polypropylene conical tube (Becton Dickinson Labware, Franklin Lakes, N.J.) using sterile techniques and sealed. The tube is then submerged in a well-controlled water bath (Exacal Ex-110 water bath Neslab Instruments, Newington, N.J.) at 68° C. for 96 hours. When a viral inactivation/removal procedure is implemented, it is important to measure that there is no alteration of protein structure and biological activities. The results of running fibronectin pasteurized as described above and freshly purified fibronectin against molecular weight standards on a standard SDS-PAGE gel showed that the pasteurized fibronectin maintained its structural integrity. The pasteurized fibronectin also demonstrated equivalent activity to freshly purified plasma fibronectin when tested for gelatin binding, cell adhesion promoting activity and chemotactic activity. The freshly purified plasma fibronectin in these tests was prepared according to the method described in Example 10. Alternatively, the lyophilized fibronectin can be submerged for 72 hours at 80° C. The solid wound healing formulations of Examples 1–5 and Example 8 can also be pasteurized after they have been sealed in the vials.

Example 12

Recombinant Fibronectin

Human or veterinary fibronectin produced by recombinant means may be utilized in the solid wound dressings of the invention in place of the plasma fibronectin purified and sterilized according to the methods described in the previous examples. Active fragments of fibronectin or modified fibronectin fragments may be utilized in alternative embodiments of the invention, using methods well known in the art. Such methods include recombinant DNA methods and chemical synthesis methods for production of proteins. For example, recombinant fibronectin polypeptide fragments can be made in bacteria or chemically synthesized. Fibronectin, fibronectin polypeptide fragments or any polypeptide compound used in the invention can be isolated from animal tissue or plasma or produced and isolated from cell culture. They may be produced and isolated from genetically altered animals, such as transgenic animals, to generate more endogenous or exogenous forms of fibronectin. Sequences of fibronectin are known to one skilled in the art, for example, as in Kornblihtt et al., EMBO J. 4:1755–1759 (1985), incorporated herein by reference, or, are available from Genbank, NCBI, NIH, and easily searchable, on the internet at http://www.ncbi.nlm.nih.gov. Publicly available databases are incorporated herein by reference in their entirety.

Representative examples of fibronectin fragments are disclosed in: U.S. Pat. No. 5,453,489, entitled "Polypeptide fragments of fibronectin which can modulate extracellular matrix assembly"; U.S. Pat. No. 5,958,874, entitled "Recombinant fibronectin-based extracellular matrix for wound healing"; and U.S. Pat. No. 5,922,676, entitled "Methods of inhibiting cancer by using superfibronectin", all of which are incorporated herein by reference in their entirety. Recombinant fibronectin fragments are also available from Takara Shuzo (Otsu, Japan).

Example 13

Wound Healing Promoters other than Fibronectin

The solid wound formulations of the invention can include other wound healing promoter having a composition similar to fibronectin, such as proteins of similar size (extracellular matrix proteins, e.g. throbospondin, laminin, vitronectin, fibrinogen) or smaller size (such as peptides including growth factors, e.g., platelet-derived growth factor). In preferred embodiments of the invention, the appropriate species-specific wound healing promoters are used, i.e., human fibronectin and/or other wound healing promoters for human applications.

Although the present invention has been described in relation to particular embodiments thereof, many other variations, modifications, and uses will become apparent to those skilled in the art. It is therefore understood that numerous variations of the invention can be made which are well within the scope and spirit of this invention as described in the appended claims.

We claim:

1. A method of producing a wound healing promoter delivery system comprising the steps of
   a) preparing a concentrated solution of fibronectin adjusted to a pH of 8.0 to 11.6:
   b) preparing a solution of an alginate salt;
   c) mixing the solution of step (a) and the solution of step (b) at a pH which is equal to or lower than the isoelectric point of fibronectin when fibronectin is positively charged to form a homogeneous mixture;

d) adding glacial acetic acid to achieve a final pH of 5.0;

e) freeze-drying the homogeneous mixture having a pH of 5.0 of step (c) to produce the solid wound healing formulation.

2. The method of claim 1, wherein the concentrated solution of fibronectin of step (a) consists of fibronectin and demineralized water.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgcggtacat atgagcctgg gttccctgac cattgct                              37

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcggatccct attaggtcac aggccgtgca gctgc                                35
```